United States Patent
Zhang

(10) Patent No.: US 9,645,068 B2
(45) Date of Patent: May 9, 2017

(54) METHOD AND SYSTEM FOR PARTICULATE FILTER LEAKAGE DETECTION

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/041,462

(22) Filed: Feb. 11, 2016

(65) Prior Publication Data

US 2017/0102311 A1  Apr. 13, 2017

Related U.S. Application Data

(63) Continuation-in-part of application No. 14/882,164, filed on Oct. 13, 2015, now Pat. No. 9,551,262.

(51) Int. Cl.
| | |
|---|---|
| *F01N 3/00* | (2006.01) |
| *G01N 15/06* | (2006.01) |
| *G01M 15/10* | (2006.01) |
| *G01N 15/00* | (2006.01) |

(52) U.S. Cl.
CPC ...... *G01N 15/0656* (2013.01); *G01M 15/106* (2013.01); *G01N 2015/0046* (2013.01)

(58) Field of Classification Search
CPC .. F01N 9/002; F01N 2900/1606; F01N 3/021; F01N 3/023; F01N 2550/04; F01N 13/008; F01N 2900/0416
USPC .......................................................... 60/277
See application file for complete search history.

(56) References Cited

U.S. PATENT DOCUMENTS

| | | | |
|---|---|---|---|
| 1,459,961 A | 6/1923 | Wheeler | |
| 6,405,577 B2 | 6/2002 | Hanashiro et al. | |
| 6,432,168 B2* | 8/2002 | Schonauer | F01N 9/002 |
| | | | 55/282.3 |
| 7,032,578 B2 | 4/2006 | Liu et al. | |
| 7,735,314 B2 | 6/2010 | Lu et al. | |
| 8,151,560 B2 | 4/2012 | Zanini-Fisher et al. | |
| 8,209,962 B2 | 7/2012 | Sun et al. | |
| 8,310,249 B2 | 11/2012 | Paterson | |
| 8,490,383 B2* | 7/2013 | Laermann | F01N 3/035 |
| | | | 60/274 |
| 8,770,016 B2 | 7/2014 | Uchiyama et al. | |
| 2010/0199839 A1* | 8/2010 | Zhang | F01N 3/0233 |
| | | | 95/23 |
| 2010/0242455 A1* | 9/2010 | Konstandopoulos | G01N 15/0618 |
| | | | 60/311 |

(Continued)

OTHER PUBLICATIONS

Zhang, Xiaogang, "System and Method for Detecting Particulate Filter Leakage," U.S. Appl. No. 14/702,988, filed May 4, 2015, 41 pages.

*Primary Examiner* — Jason Shanske
(74) *Attorney, Agent, or Firm* — Julia Voutyras; McCoy Russell LLP

(57) ABSTRACT

Methods and systems are provided for determining degradation of a particulate filter in an exhaust conduit. In one example, a method may include diverting exhaust gas to a secondary soot sensor assembly comprising a second filter downstream of a first filter, and determining degradation based on time intervals between subsequent filter regenerations of the second filter in the secondary soot sensor assembly.

19 Claims, 7 Drawing Sheets

(56) References Cited

U.S. PATENT DOCUMENTS

| | | | |
|---|---|---|---|
| 2010/0242456 A1* | 9/2010 | Konstandopoulos | G01N 15/0618 60/311 |
| 2011/0061367 A1* | 3/2011 | Laermann | F01N 3/035 60/277 |
| 2011/0072789 A1* | 3/2011 | Konstandopoulos | F01N 3/021 60/276 |
| 2011/0072801 A1* | 3/2011 | Lupescu | F01N 3/031 60/287 |
| 2011/0232362 A1 | 9/2011 | Thiagarajan et al. | |
| 2012/0090304 A1 | 4/2012 | Kotrba et al. | |
| 2012/0137659 A1* | 6/2012 | Uhrich | F01N 5/02 60/274 |
| 2013/0031967 A1 | 2/2013 | Ichimasa | |

* cited by examiner

METHOD AND SYSTEM FOR PARTICULATE FILTER LEAKAGE DETECTION

CROSS REFERENCE TO RELATED APPLICATION

The present application is a continuation-in-part of U.S. patent application Ser. No. 14/882,164, entitled "METHOD AND SYSTEM FOR PARTICULATE FILTER LEAKAGE DETECTION," filed on Oct. 13, 2015, the entire contents of which are hereby incorporated by reference for all purposes.

FIELD

The present description relates generally to the design and use of sensors for diagnosing a Diesel Particulate Filter (DPF).

BACKGROUND/SUMMARY

Engine combustion may generate particulate matter (PM) (such as soot and aerosols) that can be exhausted to the atmosphere. To enable emissions compliance, particulate matter filters, such as diesel particulate filters (DPFs) or gasoline particulate filters (GPFs) may be included in the engine exhaust, to filter out exhaust PMs before releasing the exhaust to the atmosphere. In addition, one or more soot sensors may be used to diagnose the DPFs and such soot sensors may be coupled upstream and/or downstream of the DPF.

As such, various types of soot sensors have been developed to sense soot production and release. One example approach shown by Paterson in U.S. Pat. No. 8,310,249 discloses soot sensors that collect particulate matter on charged electrodes. The soot sensor comprises opposed electrodes separated by an insulator with a gap in between to prevent current flow. When soot particles start to accumulate on the sensor, a bridge is created between the electrodes allowing current to flow. The change in current is used as an indication for soot deposition. In addition to electrode-based sensors, pressure-based soot sensors have also been developed. For example, as described by Sun et al. in U.S. Pat. No. 8,209,962, differential pressure across a particulate filter may be used for monitoring filter performance. Therein, when the differential pressure is less than a threshold, a leak in the particulate filter may be determined.

However, the inventors herein have recognized potential disadvantages with the above approaches. As one example, non-uniform or low soot deposit on the surface can occur due to biased flow distribution across the sensor surface, resulting in inaccurate voltage and current readings across the gap. Additionally, it may be difficult to reach sensor regeneration temperatures due to large flow impingement on the surface in some sensor designs. Further still, the sensors may become contaminated due to impingement of large diesel particulates or water droplets on the surface of sensor electrodes. Contamination of the sensor and interference in sensor results may also be caused by the large diesel particulates or water droplets infiltrating into the inner protection tube of the sensors. The inventors herein have identified an approach by which the issues described above may be at least partly addressed.

One example method includes, flowing exhaust gas from downstream of a first filter towards each of a first pressure sensor coupled at a first location in an exhaust pipe and a second pressure sensor coupled at a second location in a passage external to the exhaust pipe, the passage including a second filter coupled to an electric circuit, and indicating degradation of the first filter based on an interval between successive regenerations of the second filter. The first filter may be a diesel or gasoline particulate matter filter having a first, higher soot capacity, and the second filter may be a metal filter having a second, lower soot capacity. In this way, DPF diagnostics may be performed with higher accuracy and reliability without the results being corrupted by flow and soot loading distribution or impingement of water droplets.

As an example, exhaust gas may be diverted from a main exhaust pipe, downstream of a DPF, into an exhaust bypass parallel to the main exhaust pipe, outside of the main exhaust pipe via an inlet pipe. The inlet pipe may include perforations that allow water droplets and aggregated particulates to be trapped and released into the tailpipe. Downstream of the inlet pipe, the exhaust passage may be fitted with a first pressure sensor. In addition, the exhaust bypass passage may also be fitted with a second pressure sensor, downstream of a metal particle filter (MPF) coupled to an electric circuit, coupled to the exhaust bypass passage. After passing through the MPF, exhaust is returned to the main exhaust pipe via an outlet pipe. As exhaust gas diverted from the main exhaust pipe is received in the exhaust bypass, exhaust particulate materials, such as soot, may be deposited on the MPF therein, while exhaust containing soot flows unobstructed through the exhaust pipe towards the first pressure sensor. Exhaust pressure difference is calculated based on output from pressure sensors measuring pressure at the exhaust pipe and the exhaust bypass. The pressure difference between a second pressure sensor in the exhaust bypass, downstream of the MPF, and the first pressure sensor in the exhaust pipe may be used to infer a soot loading of the MPF upstream of the second pressure sensor and initiate regeneration of the MPF by closing the electric circuit coupled thereto. Further, a time interval elapsed between successive regenerations of the MPF may be monitored. As such, if the DPF in the exhaust pipe becomes degraded (such as due to age or durability issues), an increasing amount of soot may escape from the DPF, and travel onto the MPF. As a result, the MPF may have to be cleaned more frequently. Thus, based on a decrease in the time interval between successive regenerations of the metal filter in the exhaust bypass, degradation of an upstream DPF may be determined, and appropriate actions may be taken.

In this way, by diverting a portion of exhaust gas from an exhaust pipe to a soot sensor with a metal filter, located downstream of a diesel particulate filter, degradation of a particulate filter can be detected based on an amount of soot leaking from the particulate filter onto the metal filter. The technical effect of trapping soot particles on the metal filter selectively included in the exhaust bypass is that a pressure difference of exhaust between the second location at the exhaust bypass and the first location in the main exhaust pipe can be advantageously used to learn the soot load of the metal filter. As such, this reduces the need for multiple sensors for soot load estimation. The technical effect of trapping aggregated particulates and water droplets in an inlet pipe of the soot sensor, and redirecting them to the exhaust tailpipe, is that impingement of aggregated particulates and water droplets on the soot sensor is reduced, allowing for more accurate and reliable soot detection. By relying on a time interval between successive regenerations of the metal filter to detect DPF degradation, is that the diagnostics may be rendered more sensitive and less affected by variations in soot loading distribution on the metal filter. Overall, accuracy and reliability of soot sensing and diagnosing of an exhaust particulate filter is increased, enabling higher emissions compliance.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
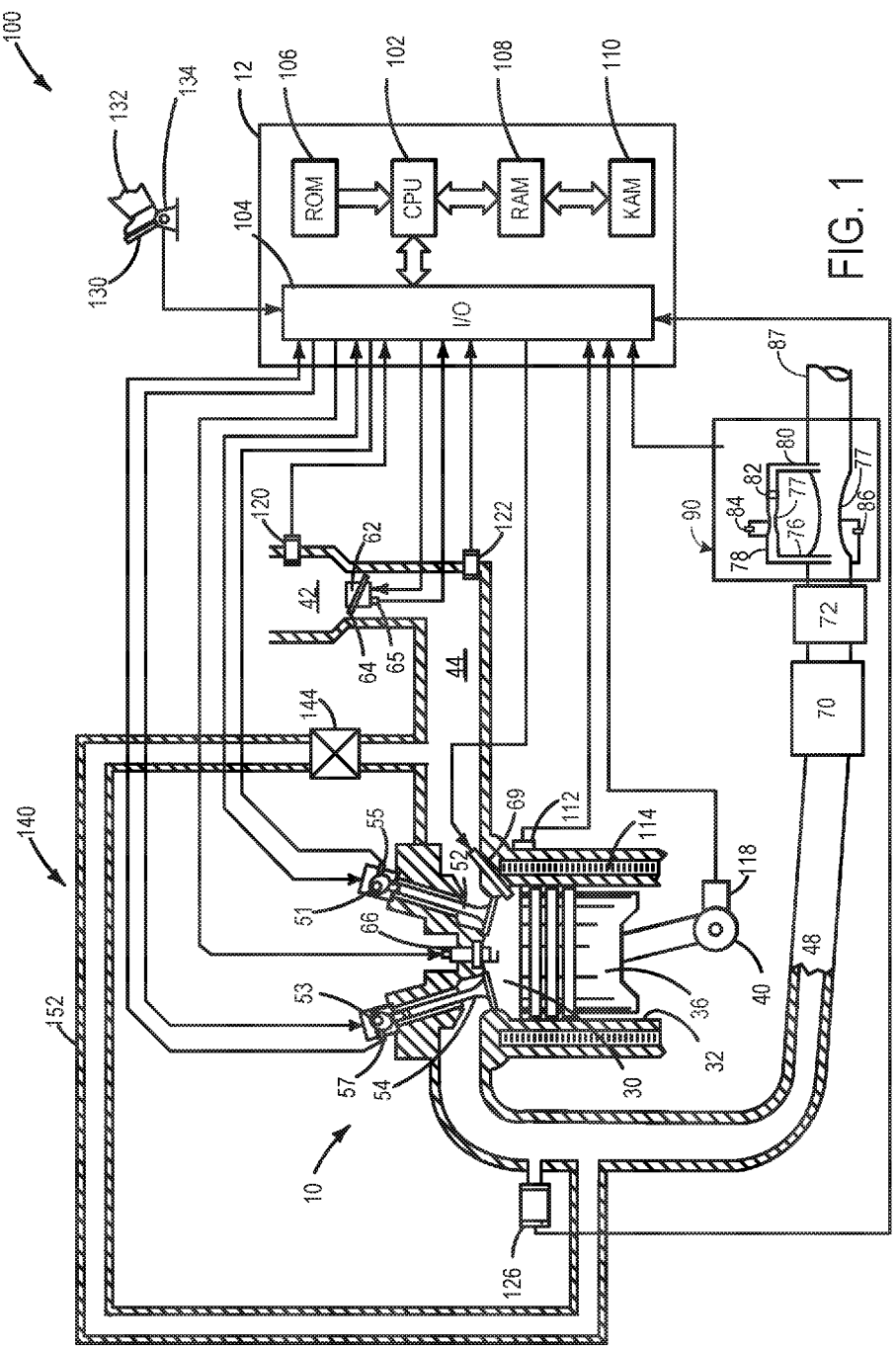
FIG. 1 shows an example engine system with an exhaust flow rate based exhaust soot sensor positioned downstream of a diesel particulate filter (DPF).
Figure 2:
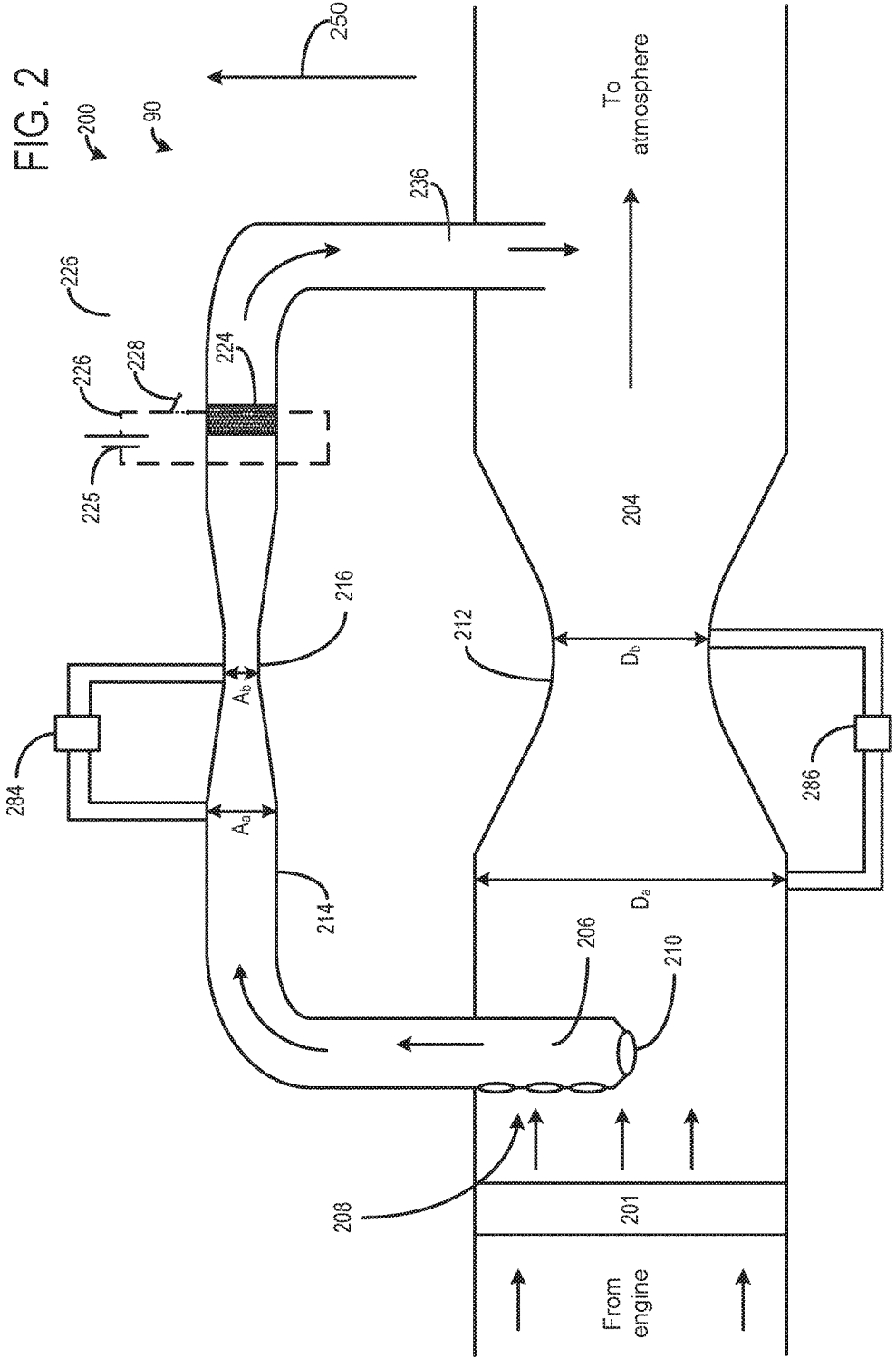
FIG. 2 shows an example embodiment of the exhaust flow rate based exhaust soot sensor assembly of FIG. 1.

The following description relates to systems and methods for determining degradation of an exhaust DPF based on an exhaust flow rate based soot sensor coupled downstream of the DPF. A vehicle system comprising of an engine configured to operate with fuels such as diesel is shown in FIG. 1. The DPF is disposed in the main exhaust pipe, and downstream from the DPF, a secondary soot sensor assembly is positioned to detect leakage of particulates from the DPF. The secondary soot sensor assembly, as shown in FIG. 2, may include an exhaust bypass parallel to the exhaust pipe, fitted with a metal filter, and an associated electric circuit. Two or more pressure sensors are provided for measuring pressure drops across respective venturi tubes of the exhaust pipe and the exhaust bypass. An engine controller is configured to perform a control routine, such as the example routine of FIG. 3, to regenerate the metal filter based on an estimated exhaust flow rate ratio between the two venturi tubes, and diagnose the DPF based on a frequency of regeneration of the metal filter. An example diagnosis is shown with reference to FIG. 4. FIG. 5 illustrates an embodiment of a pressure difference-based exhaust soot sensor assembly. An example method for diagnosing the degradation of a DPF in the exhaust pipe with the pressure difference-based soot sensor assembly is illustrated in the flow chart in FIG. 6 and an example of diagnosing a DPF based on the regeneration time of a metal filter coupled to the pressure difference-based soot sensor assembly is illustrated in FIG. 7. In this way, DPF health may be diagnosed more accurately and reliably.

FIG. 1 is a schematic diagram showing one cylinder of a multi-cylinder engine 10 in an engine system 100, which may be included in a propulsion system of an automobile. The engine 10 may be controlled at least partially by a control system including a controller 12 and by input from a vehicle operator 132 via an input device 130. In this example, the input device 130 includes an accelerator pedal and a pedal position sensor 134 for generating a proportional pedal position signal. A combustion chamber 30 of the engine 10 includes a cylinder formed by cylinder walls 32 with a piston 36 positioned therein. The piston 36 may be coupled to a crankshaft 40 so that reciprocating motion of the piston is translated into rotational motion of the crankshaft. The crankshaft 40 may be coupled to at least one drive wheel of a vehicle via an intermediate transmission system. Further, a starter motor may be coupled to the crankshaft 40 via a flywheel to enable a starting operation of the engine 10.

The combustion chamber 30 may receive intake air from an intake manifold 44 via an intake passage 42 and may exhaust combustion gases via an exhaust passage (e.g., exhaust pipe) 48. The intake manifold 44 and the exhaust pipe 48 can selectively communicate with the combustion chamber 30 via respective intake valve 52 and exhaust valve 54. In some examples, the combustion chamber 30 may include two or more intake valves and/or two or more exhaust valves.

In this example, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and exhaust valve 54 may be determined by position sensors 55 and 57, respectively. In alternative examples, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

A fuel injector 69 is shown coupled directly to combustion chamber 30 for injecting fuel directly therein in proportion to the pulse width of a signal received from the controller 12. In this manner, the fuel injector 69 provides what is known as direct injection of fuel into the combustion chamber 30. The fuel injector may be mounted in the side of the combustion chamber (as shown) or in the top of the combustion chamber, for example. Fuel may be delivered to the fuel injector 69 by a fuel system (not shown) including a fuel tank, a fuel pump, and a fuel rail. In some examples, the combustion chamber 30 may alternatively or additionally include a fuel injector arranged in the intake manifold 44 in a configuration that provides what is known as port injection of fuel into the intake port upstream of the combustion chamber 30.

Spark is provided to combustion chamber 30 via spark plug 66. The ignition system may further comprise an ignition coil (not shown) for increasing voltage supplied to spark plug 66. In other examples, such as a diesel, spark plug 66 may be omitted.

The intake passage 42 may include a throttle 62 having a throttle plate 64. In this particular example, the position of throttle plate 64 may be varied by the controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by a throttle position signal. The intake passage 42 may include a mass airflow sensor 120 and a manifold air pressure sensor 122 for sensing an amount of air entering engine 10.

An exhaust gas sensor 126 is shown coupled to the exhaust pipe 48 upstream of both an exhaust gas recirculation system 140 and an emission control device 70 according to a direction of exhaust flow. The sensor 126 may be any suitable sensor for providing an indication of exhaust gas air-fuel ratio such as a linear oxygen sensor or UEGO (universal or wide-range exhaust gas oxygen), a two-state oxygen sensor or EGO, a HEGO (heated EGO), a $NO_x$, HC, or CO sensor. In one example, upstream exhaust gas sensor 126 is UEGO configured to provide output, such as a voltage signal, that is proportional to the amount of oxygen present in the exhaust. Controller 12 converts oxygen sensor output into exhaust gas air-fuel ratio via an oxygen sensor transfer function.

An exhaust gas recirculation (EGR) system 140 may route a desired portion of exhaust gas from the exhaust pipe 48 to the intake manifold 44 via an EGR passage 152. The amount of EGR provided to the intake manifold 44 may be varied by the controller 12 via an EGR valve 144. Under some conditions, the EGR system 140 may be used to regulate the temperature of the air-fuel mixture within the combustion chamber, thus providing a method of controlling the timing of ignition during some combustion modes.

The emission control device 70 is shown arranged along the exhaust pipe 48 downstream of the exhaust gas sensor 126. The device 70 may be a three way catalyst (TWC), $NO_x$ trap, various other emission control devices, or combinations thereof. In some examples, during operation of the engine 10, the emission control device 70 may be periodically reset by operating at least one cylinder of the engine within a particular air-fuel ratio.

A particulate filter 72 is shown arranged along the exhaust pipe 48 downstream of the emission control device 70. Exhaust gas treated by emission control device 70 and particulate filter 72 is released into the atmosphere through tailpipe 87. The particulate filter 72 may be a diesel particulate filter or a gasoline particulate filter. A substrate of the particulate filter 72 may be made of ceramic, silicon, metal, paper, or combinations thereof. During operation of the engine 10, particulate filter 72 may capture exhaust particulate matter (PMs), such as ash and soot (e.g., from unburned hydrocarbons) in order to reduce vehicle emissions. The soot may clog the surfaces of the particulate filter thereby creating an exhaust backpressure. The exhaust backpressure may negatively influence the engine performance. Once the particulate filter 72 becomes fully loaded with soot (e.g., soot load on the particulate filter exceeds a soot load threshold), the backpressure may be too high for proper exhaust expulsion. Work used to expel exhaust from the engine 10 increases in order to overcome the backpressure described above. In order to avoid high backpressure, an engine 10 may periodically regenerate the filter either passively or actively.

Passive regeneration may occur when an engine load exceeds a threshold load causing an exhaust temperature to rise. As the exhaust temperature increases beyond a threshold temperature (e.g., 450° C.), the soot on the particulate filter 72 may combust. Therefore, passive regeneration occurs without alterations to engine operations. Conversely, active regeneration occurs via the controller 12 signaling for alterations to engine operations in order to increase exhaust temperatures (e.g., late injection, secondary injection, throttling, exhaust recirculation, spark retard, and/or a decrease in air/fuel ratio) independent of the engine load. For example, the controller may send signals to a fuel injector to increase the pulse-width of the fuel injection, and enrich the combustion air-fuel ratio (relative to stoichiometry). As another example, the controller may send signals to an electromechanical actuator coupled to the intake throttle to move the throttle valve towards a more open position, thereby increasing airflow to the engine. In still other examples, valve timing may be adjusted (e.g., via cam adjustments) to increase positive valve overlap.

As the soot burns during either passive or active regeneration, the particulate filter temperature increases to a higher temperature (e.g., 1400° C.). Extended engine operation at the elevated regeneration temperature may expedite degradation of the particulate filter 72. Degradation may include the particulate filter 72 developing a leak (e.g., crack) and/or a hole, which may cause soot to escape from the filter, and flow further downstream into the exhaust pipe 48, increasing vehicle emissions. As such, this can cause an engine to be emissions non-compliant.

Other factors contributing to particulate filter degradation include vehicle vibrations and lubricating oil ash. Vehicle vibrations may degrade fragile components within the particulate filter 72 due to expansion of the components (i.e., decreased stability) caused by exposure of the particulate filter 72 to high temperatures. Lubricating oil ash may contain metal oxides which can react with the particulate filter 72 and form phases (e.g., portions of the particulate filter degrade while other portions remain functional), ultimately degrading at least a portion of the particulate filter.

Diagnosis of particulate filter 72 may be enabled using a secondary soot sensor assembly and associated pressure or flow sensors. A secondary soot sensor assembly 90 is shown arranged along the exhaust pipe 48 downstream of the particulate filter 72. The secondary soot sensor assembly 90 comprises an inlet pipe 76 positioned partially within the exhaust pipe 48, at an end of the secondary soot sensor assembly 90 nearest the particulate filter 72. The secondary soot sensor assembly 90 further comprises an outlet pipe 80 positioned partially within the exhaust pipe 48, at an opposite end of the secondary soot sensor assembly 90 farthest away from the particulate filter 72.

The inlet pipe 76 and the outlet pipe 80 are fluidly coupled to the exhaust pipe 48 such that at least a portion of exhaust gas flows from the exhaust pipe 48 into the inlet pipe 76, at a location downstream of particulate filter 72, and then from the outlet pipe 80 back into the exhaust pipe 48, at a location upstream of an exhaust tailpipe. The part of the exhaust pipe 48 between the inlet pipe 76 and the outlet pipe 80 is fitted with a first venturi, or configured as a first venturi tube 77. Further, the flow assembly 90 includes an exhaust bypass 78 fitted with a second venturi, or configured as a second venturi tube 77. The first venturi tube is a larger venturi tube with a higher motive flow rate, while the second venturi tube is a smaller venturi tube with a lower motive rate. In one example, the exhaust bypass 78 and exhaust pipe 48 may be substantially parallel and may be made of the same material. However, in alternate examples, the exhaust pathways may be substantially parallel and/or may have different geometrical structures.

The exhaust bypass 78 includes a metal filter 82 fitted downstream from the venturi tube. The metal filter 82 may be smaller than the particulate filter 72 (that is, smaller in diameter, in width, and/or length). However, the porosity of the metal filter 82 may be the same as or less than the porosity of particulate filter 72. Metal filter 82 may be coupled to an electric circuit (shown in FIG. 2), the electric circuit in turn electronically coupled to controller 12.

In this way, a portion of exhaust gas from the exhaust pipe 48 may flow along exhaust pipe 48 and first venturi tube 77 while a remaining portion of the exhaust gas flows into exhaust bypass passage 78 and second venturi tube 79 via inlet pipe 76, the inlet pipe 76 converging with the bypass passage at a location external to the exhaust pipe 48. Further, the remaining portion of exhaust gas flowing through the second venturi tube 79 may then return into the exhaust pipe 48, at a location downstream of metal filter 82, via an outlet pipe 80, the bypass passage 78 converging into the outlet pipe 80 at a location downstream of the metal filter 82 and external to the exhaust pipe 48. A detailed embodiment of the secondary soot sensor assembly 90 is described with reference to FIG. 2.

The secondary soot sensor assembly 90 may be used to determine degradation of the particulate filter 72. In particular, soot loading of metal filter 82 may be estimated based on a ratio of the exhaust flow rates through the first and second venturi tubes fitted on the exhaust pipe 48 and exhaust bypass 78 respectively. As the soot load on the metal filter 82 increases, an exhaust flow through the second venturi 79 in the bypass 78 decreases relative to exhaust flow through the first venturi 77 in the exhaust passage. Exhaust flow rates may be calculated based on the relative pressure drop across the first and second venturi tubes of the exhaust pipe and the exhaust bypass, respectively. A pressure sensor 86 may be coupled to the exhaust pipe venturi tube 77 while a pressure sensor 84 may be coupled to the exhaust bypass venturi tube to estimate the flow rates of the exhaust passing through them respectively. In particular, the pressure sensors may be coupled to the converging section or motive inlets of the venturi tubes. The pressure sensor 84 is located upstream of the metal filter 82. Based on the soot loading, an electric current may be passed through the metal filter 82 to regenerate the filter. Due to the smaller size of the metal filter, the filter may be periodically regenerated. Based on the periodicity of the regeneration, relative to a threshold, leakage of soot from the particulate filter 72 may be determined, as elaborated with reference to FIGS. 2 and 3.

The controller 12 is shown in FIG. 1 as a microcomputer, including a microprocessor unit 102, input/output ports 104, an electronic storage medium for executable programs and calibration values shown as read only memory chip 106 (e.g., non-transitory memory) in this particular example, random access memory 108, keep alive memory 110, and a data bus. The controller 12 may receive various signals from sensors coupled to the engine 10, in addition to those signals previously discussed, including measurement of pressure or exhaust flow rate through the venturi tubes from pressure sensors 84 and 86 on the secondary soot sensor assembly 90, measurement of inducted mass air flow (MAF) from the mass air flow sensor 120; engine coolant temperature (ECT) from a temperature sensor 112 coupled to a cooling sleeve 114; an engine position signal from a Hall effect sensor 118 (or other type) sensing a position of crankshaft 40; throttle position from a throttle position sensor 65; and manifold absolute pressure (MAP) signal from the sensor 122. An engine speed signal may be generated by the controller 12 from crankshaft position sensor 118. Manifold pressure signal also provides an indication of vacuum, or pressure, in the intake manifold 44. Note that various combinations of the above sensors may be used, such as a MAF sensor without a MAP sensor, or vice versa. During engine operation, engine torque may be inferred from the output of MAP sensor 122 and engine speed. Further, this sensor, along with the detected engine speed, may be a basis for estimating charge (including air) inducted into the cylinder. In one example, the crankshaft position sensor 118, which is also used as an engine speed sensor, may produce a predetermined number of equally spaced pulses every revolution of the crankshaft.

The storage medium read-only memory 106 can be programmed with computer readable data representing non-transitory instructions executable by the processor 102 for performing the methods described below as well as other variants that are anticipated but not specifically listed.

The controller 12 receives signals from the various sensors of FIG. 1 and employs the various actuators of FIG. 1 to adjust engine operation based on the received signals and instructions stored on a memory of the controller 12. In one example, the controller 12 closes a switch on the electric circuit (shown in FIG. 2) used for regeneration of the secondary soot sensor assembly 90. In another example, the controller 12 alters an engine operation to limit torque output of a vehicle in response to increased frequency of metal filter 82 regeneration in the secondary soot sensor assembly 90

FIG. 2 shows a schematic view of an example embodiment of an exhaust flow rate based secondary soot sensor assembly 200. In one example, assembly 200 is an embodiment of assembly 90 of FIG. 1 and therefore may share common features and/or configurations as those already described for secondary assembly 90. Secondary soot sensor assembly 200 is fluidly coupled to exhaust pipe 204. Exhaust pipe 204 includes a first particulate filter 201. In one example, the first particulate filter is a larger diesel or gasoline particulate matter filter having a higher soot capacity. The secondary soot sensor assembly 200 is coupled to exhaust pipe 204 downstream of first filter 201. For example, first filter 201 and exhaust pipe 204 may be examples of particulate filter 72 and exhaust pipe 48 of FIG. 1.

Exhaust gas flowing from the engine passes through the first filter 201 and reaches the secondary soot sensor assembly 200 located further downstream along the exhaust pipe 204. Solid line arrows indicate a direction of the exhaust flow in the exhaust pipe 204 past the DPF. At least a portion of the exhaust gas flowing through the exhaust pipe 204 is diverted into the secondary soot sensor assembly 200 via an inlet pipe 206. The inlet pipe leads to an exhaust bypass passage 214 external to the exhaust pipe 204. The bypass passage 214 ends in an outlet pipe 236 external to the exhaust pipe 204. The outlet pipe 236 directs the flow of exhaust gas back to the exhaust pipe 204 downstream of the inlet pipe 206.

A portion of each of the inlet pipe 206 and outlet pipe 236 is coupled internally to the exhaust pipe 204 and a remaining portion of each of the inlet pipe 206 and outlet pipe 236 is coupled externally to the exhaust pipe 204. The inlet pipe 206 extends though the exterior wall of the exhaust pipe 204 and into the interior of the exhaust pipe 204. In one example, the portion of inlet pipe 206 and outlet pipe 236 internal to exhaust pipe 204 is smaller than the remaining portion of inlet pipe 206 and outlet pipe 236 external to exhaust pipe 204, respectively. In the depicted example outlet pipe 236 has a shorter length relative to inlet pipe 206. In addition, the portion of outlet pipe 236 that dips internal to exhaust pipe 204 is smaller than the portion of inlet pipe 206 that dips internal to exhaust pipe 204.

The inlet pipe 206 comprises a plurality of perforations 208 on a side of the inlet pipe within the exhaust pipe 204 and proximate to the first filter 201. The perforations 208 face the first filter 201 and the direction of the oncoming exhaust gas flow. There are no perforations on the opposite side (wall) of the inlet pipe 206. As a result of this configuration, aggregated particulates and water droplets in the exhaust may impinge the inner face of the inlet pipe, and be released into the exhaust pipe, without affecting a sensitivity of the soot sensing assembly. The centerline of the inlet pipe 206 is perpendicular to the center line of the exhaust pipe 204 and the perforations 208 are completely situated inside the exhaust pipe 204. There may be more perforations configured on the inlet pipe 206 as compared to the outlet pipe 236. In one example, there may be no perforations on the outlet pipe 236, as depicted. A perforation 210 is located at the bottom of the inlet pipe 206 within the exhaust pipe 204. The perforation 210 is arranged perpendicular to the perforations 208 on inlet pipe 206. A diameter of the perforations on the inlet tube side wall may be adjusted to enable conglomerated particulates and water droplets in the exhaust gas to impinge on a side of the inlet pipe within the exhaust pipe and distal to the first filter 201, the conglomerated particulates being released from the inlet pipe into the exhaust pipe via a perforation 210 on a bottom of the inlet pipe. In this way, the conglomerated particulates and water droplets can then be released from the inlet pipe 206 into the exhaust pipe via a perforation 210 on a bottom of the inlet pipe reducing contamination of the exhaust bypass passage 214 and metal filter 224 and thereby improving the accuracy of the secondary soot sensor assembly 200.

The portion of the exhaust pipe 204 between the inlet pipe 206 and the outlet pipe 236 may be fitted with a first venturi, or configured as a first venturi tube 212 (as shown). A first pressure sensor 286 may be coupled between the motive inlet and neck of the first venturi tube 212 for estimating a flow rate of exhaust through the first venturi tube 212. In an alternate embodiment, a flow sensor may be coupled to the first venturi for sensing an exhaust flow rate there-through. Further still, the exhaust flow rate through the first venturi tube may be inferred based on engine operating conditions and the geometry of the first venturi tube. The bypass passage 214 may likewise be fitted with a second venturi tube 216 (as shown) at a position substantially equidistant from the inlet pipe 206 and outlet pipe 236. The second venturi tube 216 may be smaller in size compared to the first venturi tube 212. For example, the second venturi tube may have one or more or all of a narrower neck, a narrower motive inlet diameter, and a narrower motive outlet diameter than the first venturi tube. Consequently, exhaust may flow through the first venturi tube at a higher flow rate than through the second venturi tube.

A pressure sensor 284 may be coupled between the motive inlet and neck of the second venturi tube 216 for estimating the exhaust flow rate through the second venturi tube 216. In one example, flow of exhaust through the second venturi tube may be advantageously harnessed by drawing a vacuum at the neck of the venturi tube, the vacuum stored for later use (e.g., during purging), or applied to a vacuum-actuated engine actuator, such as a brake booster.

A part of the exhaust gas may flow from the exhaust pipe 204 into an inlet pipe 206 (shown by single solid arrow pointing upwards), and from the inlet pipe 206 into the exhaust bypass passage 214. The direction of flowing exhaust gas through the inlet pipe 206 and the outlet pipe 236 is substantially perpendicular to a direction of exhaust flow through each of the exhaust pipe 204, and the first and second venturi. The portion of the inlet pipe 206 located outside of the exhaust pipe 204 has a lower temperature compared to the part of the inlet pipe 206 located inside the exhaust pipe 204. The temperature drop may cause the water vapor in the exhaust gas to condense on the surfaces of inlet pipe 206. The condensate may fall through the perforation 210 back into the exhaust pipe 204 thereby reducing the entry of water droplets into the secondary soot sensor assembly 200.

Exhaust flow rates in the exhaust pipe 204 and exhaust bypass passage 214 are calculated based on the geometry of the systems and pressure drops through the respective venturi tubes. Exhaust flow rate through the first venturi tube 212 may be calculated via Equation 1 depicted below.

$$Q_o = C \sqrt{\frac{2\Delta p}{\rho} * \frac{D_a}{\sqrt{\left(\frac{D_a}{D_b}\right)^2 - 1}}} \tag{1}$$

In equation 1, $Q_0$ represents a flow rate of exhaust gas through the exhaust pipe 204. $\Delta p$ is the pressure difference between the venturi tube 212 and the region of the exhaust pipe 204 upstream of the venturi tube 212 as estimated by pressure sensor 286. Density ($\rho$) is estimated for exhaust gas flowing through the exhaust pipe 204 based on current engine conditions (e.g., intake air temperature, load, pressure, etc.). A density ($\rho$) of the exhaust gas may be calculated based on a manipulation of the ideal gas law. Furthermore, under confines of the ideal gas law, the density of the exhaust gas may be assumed constant (e.g., an incompressible gas). The density calculated is dependent upon a pressure and temperature of the exhaust gas, where the density increases as the pressure increases and the density decreases as the temperature increases. $D_a$ and $D_b$ represent cross-sectional areas of the motive inlet and the neck of the first venturi tube 212 respectively, as indicated in the FIG. 2. The pressure sensor 286 is coupled across from the regions with cross-sections $D_a$ and $D_b$ respectively. C represents a constant calculated based on the geometry of the first venturi tube 212. The constant C being dependent on a venturi tube geometry is characteristic of the venturi tube and this value may vary for different venturi tubes.

Calculating the flow rate, $Q_1$ through the second venturi tube 216 is similar and therefore, description of calculating the flow rate through the first venturi tube 212 may be applied to the second venturi tube 216 as well. For the second venturi tube 216, the cross-sectional areas of the motive inlet and the neck of the first venturi tube 212, $A_A$ and $A_b$ respectively are used. In addition, the pressure difference ($\Delta p$) between the motive inlet and the neck of the first venturi tube of the venturi tube 216, as estimated by the pressure sensor 286 is used. The constant C to be used for the second venturi tube may be different from the constant used for the first venturi tube, depending on their geometries.

In order to calculate the flow rate, pressure difference ($\Delta p$) and air density ($\rho$) are measured, while C, $D_a$ ($A_a$), and $D_b$ ($A_b$) are known variables based on defined geometries. As can be seen from equation 1, flow rate is proportional to one or more of the p and $\rho$. Hence the flow rate through a venturi tube, increases as pressure difference $\Delta p$, increases and decreases as density, p, increases. The ratio of exhaust flow rates though the first venturi tube 212 and the second venturi tube 216 is given by Equation 2 as depicted below $$CI = Q_0/Q_1 \qquad (2)$$

In equation 2, CI represents a ratio between exhaust flow rate $Q_0$ though the first venturi tube 212 and the exhaust flow rate $Q_1$ though the second venturi tube 216. Given the geometries of the exhaust pipe 204 and the exhaust bypass passage 214, $Q_1$ is always lower than $Q_0$.

A second metal particulate filter (MPF) 224 is affixed across the bypass passage 214 downstream from the venturi tube 216. The metal filter faces perpendicular to the direction of exhaust flow into the bypass passage 214 such that the exhaust gas flows through the metal filter 224. In one example, the second filter 224 is smaller compared to the first filter 201 and is located outside of the exhaust pipe 204 while first filter 201 is housed within exhaust pipe 204. The second filter 224 is coupled on the bypass passage 214 between a motive outlet of the second venturi tube 216 and the outlet pipe 236. The metal filter surface may be flat and/or disk-shaped, comprising of metal fibers. The metal filter effectively traps soot and particulate matter in its pores as exhaust gas flows through the bypass passage 214 to outlet pipe 236. The portion of the exhaust gas passing through the exhaust pipe 204 without entering the inlet pipe 206, passes through without flowing through any filter.

Metal particulate filter 224 is electrically coupled to a circuit 226 including a switch 228 and a source of electricity 225. In the depicted example, the source of electricity 225 includes a battery (or battery pack). The switch 228 may be alternated between an open position, indicated by a solid line, and a closed position 230, indicated by a dotted line. When the switch 228 is moved to the closed position 230, such as when second metal filter regeneration conditions are met, the circuit 226 is completed and an electric current (drawn from the source of electricity 225) can pass through the metal filter 224 causing an increase in temperature at the filter. The heat generated may be used to regenerate the metal filter 224 by burning off soot captured on the metal filter surface over a period. At all times other than during metal filter 224 regeneration, the switch 228 may be left in the open position.

As soot accumulates in the metal filter over a period of time, exhaust backflow increases, which decreases $Q_1$. Consequently, exhaust flow ratio increases as $Q_1$ decreases. Regenerating the second metal filter is based on the exhaust flow ratio between exhaust flow rate $Q_0$ though the first venturi tube 212 and the exhaust flow rate $Q_1$ though the second venturi tube 216. Specifically, a controller may initiate regeneration of the second filter when the exhaust flow ratio is indicative of a higher than threshold ratio between the two exhaust flow rates, and terminate regeneration of the second filter when the exhaust flow ratio is indicative of a lower than threshold ratio between the two exhaust flow rates. Thus, in response to the exhaust flow rate $Q_0$ though the first venturi tube 212 and the exhaust flow rate $Q_1$ though the second venturi tube 216, particularly when exhaust flow ratio reaches a predetermined first (upper) threshold, the engine controller may send a signal to actuate switch 228 of the electric circuit 226 to the closed position. On closing the switch 228, the electric circuit is completed and current flows through the metal filter 224 causing an increase in temperature. The heat generated starts burning away the soot deposit and regenerating the metal filter 224. The exhaust flow ratio CI is simultaneously estimated from the exhaust flow rate $Q_0$ though the first venturi tube 212 and the exhaust flow rate $Q_1$ though the second venturi tube 216.

As the soot deposit decreases, exhaust flow ratio CI starts decreasing. When exhaust flow ratio reaches a pre-determined second (lower) threshold, it may be inferred that the metal filter 224 has been sufficiently regenerated and the controller sends a signal to actuate switch 228 of the circuit 226 to the open position, stopping further flow of current, and filter regeneration.

As such, when the DPF is degraded, more soot travels downstream though the exhaust pipe 204 to the secondary soot sensor assembly 200. As a result, soot accumulates on the metal filter 224 at an increased rate, and regeneration of the metal filter 224 has to be carried out more frequently. Thus by monitoring an interval between successive regenerations of the metal filter, degradation or leakage of the DPF can be determined.

FIGS. 1 and 2 show example configurations of the soot sensing assembly with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example.

Figure 3:
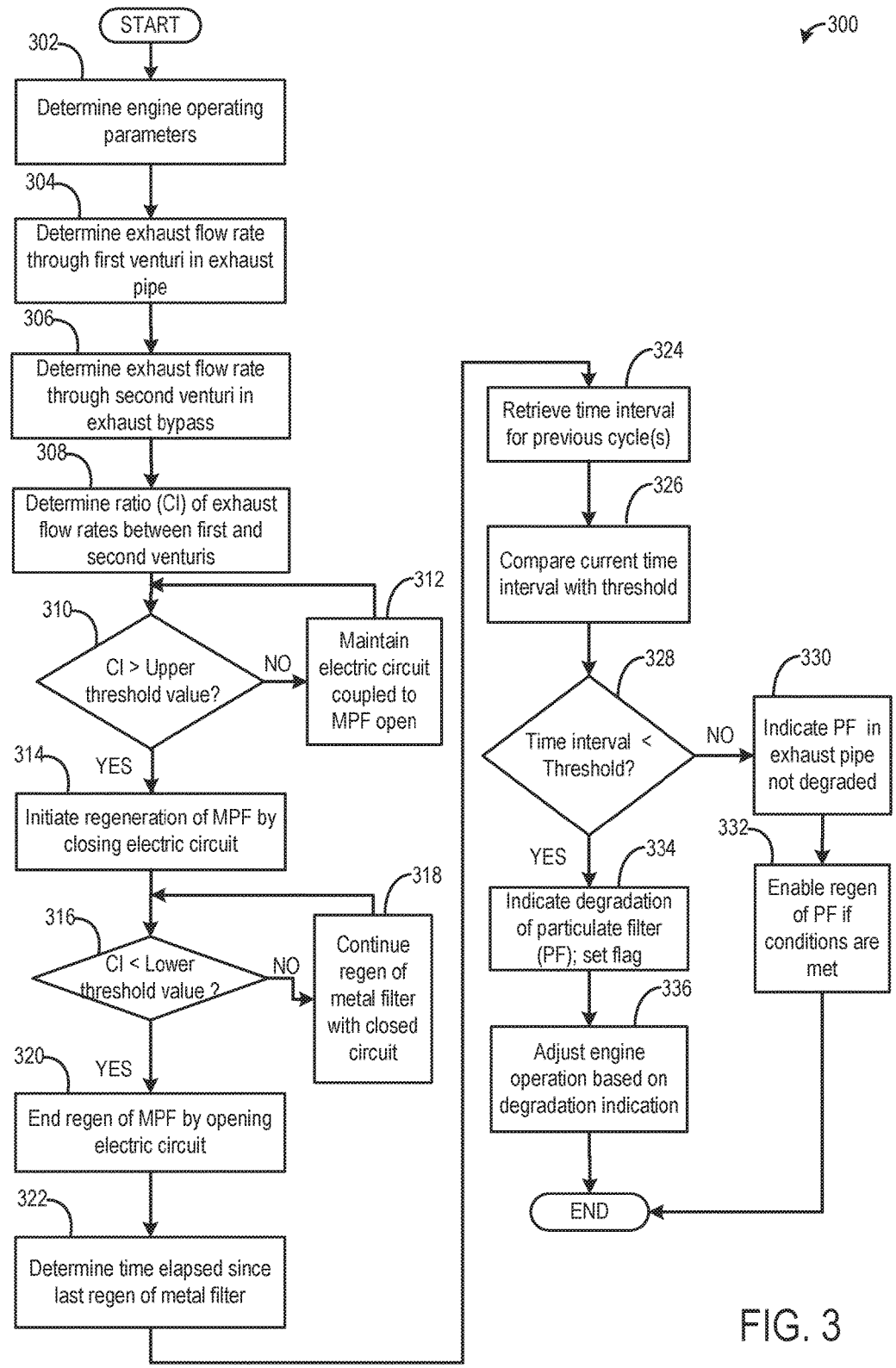
FIG. 3 shows a flow chart illustrating a method that may be implemented for diagnosing degradation of a DPF in the exhaust pipe based on exhaust flow rate ratio between two venturi tubes.

FIG. 3 illustrates an example method 300 for diagnosing degradation of an exhaust particulate filter in an engine exhaust passage. Instructions for carrying out method 300 and the rest of the methods included herein may be executed by a controller based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

At 302, the routine includes estimating and/or measuring current engine operating parameters. Parameters assessed may include, for example, engine load, engine speed, vehicle speed, manifold vacuum, throttle position, exhaust pressure, exhaust air/fuel ratio, etc.

At 304, the routine determines the exhaust gas flow rate through the first venturi tube in the exhaust pipe. The flow rate is estimated based on the geometry of the system and pressure drop through the exhaust pipe venturi tube. Exhaust flow rate through the first venturi tube may be calculated using Equation 1, where the pressure drop is measured using a pressure sensor (such as pressure sensor 286 in FIG. 2) coupled across the motive inlet and the neck of the first venturi tube.

At 306, the routine determines the exhaust gas flow rate through the second venturi tube in the exhaust bypass. Similar to the first venturi tube, the flow rate is estimated based on the geometry of the system and pressure drop through the exhaust bypass passage venturi tube. Exhaust flow rate through the exhaust bypass passage venturi tube may be calculated using Equation 1, where the pressure drop is measured using a pressure sensor (such as pressure sensor 284 in FIG. 2) coupled across the motive inlet and the neck of the second venturi tube.

At 308, the routine includes determining a ratio (CI) of the exhaust flow rates between the exhaust pipe and exhaust bypass passage venturi tubes. The ratio (CI) may be estimated by using Equation 2. The first venturi is larger than the second venturi, and the ratio of flow rates through the first and second venturi is based on a first pressure at a motive inlet of the first venturi relative to a second pressure at the motive inlet of the second venturi. As such, as soot deposits on the metal filter located on the exhaust bypass passage downstream from the second venturi tube, exhaust backflow may increase and an exhaust flow ratio (CI) between the two venturi tubes may proportionally increase.

At 310, the routine includes determining if the exhaust flow ratio (CI) is greater than a pre-determined threshold. Herein, the threshold is a first upper threshold above which the metal filter in the exhaust bypass passage may have to be regenerated. The upper threshold may be based on engine operating conditions, such as engine load and/or the soot load of the first filter. In one example, the upper threshold for regenerating the second metal filter may be a function of an upper threshold for regenerating the first filter. Alternatively, the upper threshold may be a fixed value based on the specific configuration and dimensions of the metal filter. If CI is lower than the upper threshold, the routine proceeds to 312 to maintain the switch of the electric circuit in the open position. In addition, the controller continues monitoring the exhaust ratio between the two venturi tubes. When the switch of the electric circuit coupled to the second metal filter in the second pathway is in the open position, no current flows through the circuit, and regeneration of the metal filter is not initiated.

If the exhaust flow ratio (CI) between the two venturi tubes is higher than the upper threshold, the routine proceeds to 314 where the controller (such as controller 12 of FIG. 1) sends a signal to actuate the switch of the electric circuit coupled to the metal filter to a closed position in order to complete the circuit. On circuit completion, electricity (that is, an electric current) flows through the metal filter and regeneration of the filter starts. In this way, regeneration of the second filter is carried out responsive to a ratio of exhaust flow rate through the first venturi tube relative to the second venturi tube being higher than an upper threshold. As described above, by closing the circuit, the metal filter is heated electrically, effectively burning soot deposited on the filter. The regenerating of the second filter is continued with the switch of the electric circuit closed and by flowing electricity (current) through the second filter until the exhaust flow ratio between the first and second venturi tubes is lower than a lower threshold. The lower threshold may be a function of the upper threshold, and may reflect a condition where the second filter is sufficiently clean. Thus, the switch may remain in the closed position until regeneration of the second metal filter is completed. During the regeneration process, the exhaust flow ratio between the venturi tubes (CI) decreases proportionally with the reduction of the soot load.

At 316, the routine includes determining if the exhaust flow ratio (as based on the output of the pressure sensors) is less than a pre-determined second (lower) threshold. The lower threshold, like the upper threshold, may be adjusted based on engine operating conditions, such as a soot load of the first filter, as well as the porosity of the second smaller metal filter. If the exhaust flow ratio is higher than the second threshold flow ratio value, the routine moves to 318 where the controller continues with the regeneration process by maintaining the switch, and consequently the circuit closed.

Upon confirming that exhaust flow ratio is lower than the second threshold, at 320, the regeneration process may be stopped. Therein, the controller may send a signal to actuate the switch of the electric circuit coupled to the metal filter to an open position. As a result, current stops flowing through the circuit, terminating the regeneration. In this way, regenerating the second filter includes closing a switch of the electric circuit and flowing electricity through the second filter until ratio of flow rates through the first and second venturi is lower than a lower threshold.

At 322, the routine includes determining a time elapsed since the last regeneration of the metal filter. As such, this corresponds to a time interval between the last regeneration and a current regeneration of the metal filter. Alternately, this may be determined as a time elapsed since a last opening of the switch. The interval is measured from initiation of a first regeneration event of the second filter to initiation of a second, immediately subsequent regeneration event of the second filter, with no regenerations in between. In one example, a timer may be started when a regeneration of the filter is completed (such as when the switch is opened at 320), the timer stopped when a subsequent regeneration of the filter is completed (such as when the switch is opened during a subsequent iteration of method 300). The time intervals between successive regenerations may be stored in the memory of the controller.

At 324, the routine includes retrieving the time interval for the previous cycle. In an alternate example, an average duration between successive regeneration events of the metal filter over a duration or distance of vehicle operation, or a threshold number of engine cycles may be determined. The number of previous cycles used to determine the average time interval may be varied.

At 326, the routine includes comparing the current time interval (determined at 322) to a threshold time interval, the threshold including the time interval for the previous cycle (or the retrieved average time interval) as determined at 324. The interval is measured from initiation of a first regeneration event of the second filter to initiation of a second, immediately subsequent regeneration event of the second filter. During standard engine operation and when the DPF operates without degradation, the amount of soot deposited on the metal filter after each regeneration cycle may be comparable, resulting in intermittent regenerations with a symmetric periodicity. However, with age and durability issues, when the DPF becomes degraded, an increasing amount of soot may escape uncaptured by the DPF, and travel downstream through the exhaust pipe. This increased soot load may partly accumulate on the metal filter and as a result, the metal filter may have to be regenerated (cleaned) more frequently.

At 328, the routine determines if the current time interval is less than the threshold. If the time interval is not less than the threshold, it may be determined at 330 that the DPF is not degraded. At 332, in response to the time interval being greater than a threshold time interval, regeneration of the particulate filter in the engine exhaust conduit may be initiated when particulate filter regeneration conditions are met via one or more of a retarding spark and decreasing an air/fuel ratio.

If the time interval is less than the threshold, the routine proceeds to 334 to indicate degradation of the DPF. For example, it may be indicated that there is a leak, hole, crack, or other damage to the DPF. The indicating may include setting a flag or a diagnostic code, or activating a malfunction indicator lamp in order to notify the vehicle operator that the DPF is degraded and have to be replaced. In this way, degradation of a DPF is indicated responsive to the interval between successive regenerations of a second filter, located downstream of the DPF, being lower than a threshold duration.

At 336, in response to the indication of degradation, the controller may adjust the operation of one or more engine actuators to adjust engine operation. As one example, in response to the indication of degradation, the controller may limit an engine speed or load (e.g., by reducing an opening of an intake throttle), limit an engine torque output, and/or reduce boost pressure (e.g., by opening, a wastegate coupled to an exhaust turbine or a bypass valve coupled to an intake compressor).

In this way, engine operation may be adjusted based on degradation of a particulate filter positioned in an engine exhaust conduit, upstream of a first venturi, the degradation determined based on a time interval between a first regeneration and a second regeneration of a metal filter positioned downstream of a second venturi in an exhaust bypass, the exhaust bypass coupled across the first venturi and external to the exhaust passage. The first and second regeneration are based on a ratio of flow rates across the first and second venturi.

Figure 4:
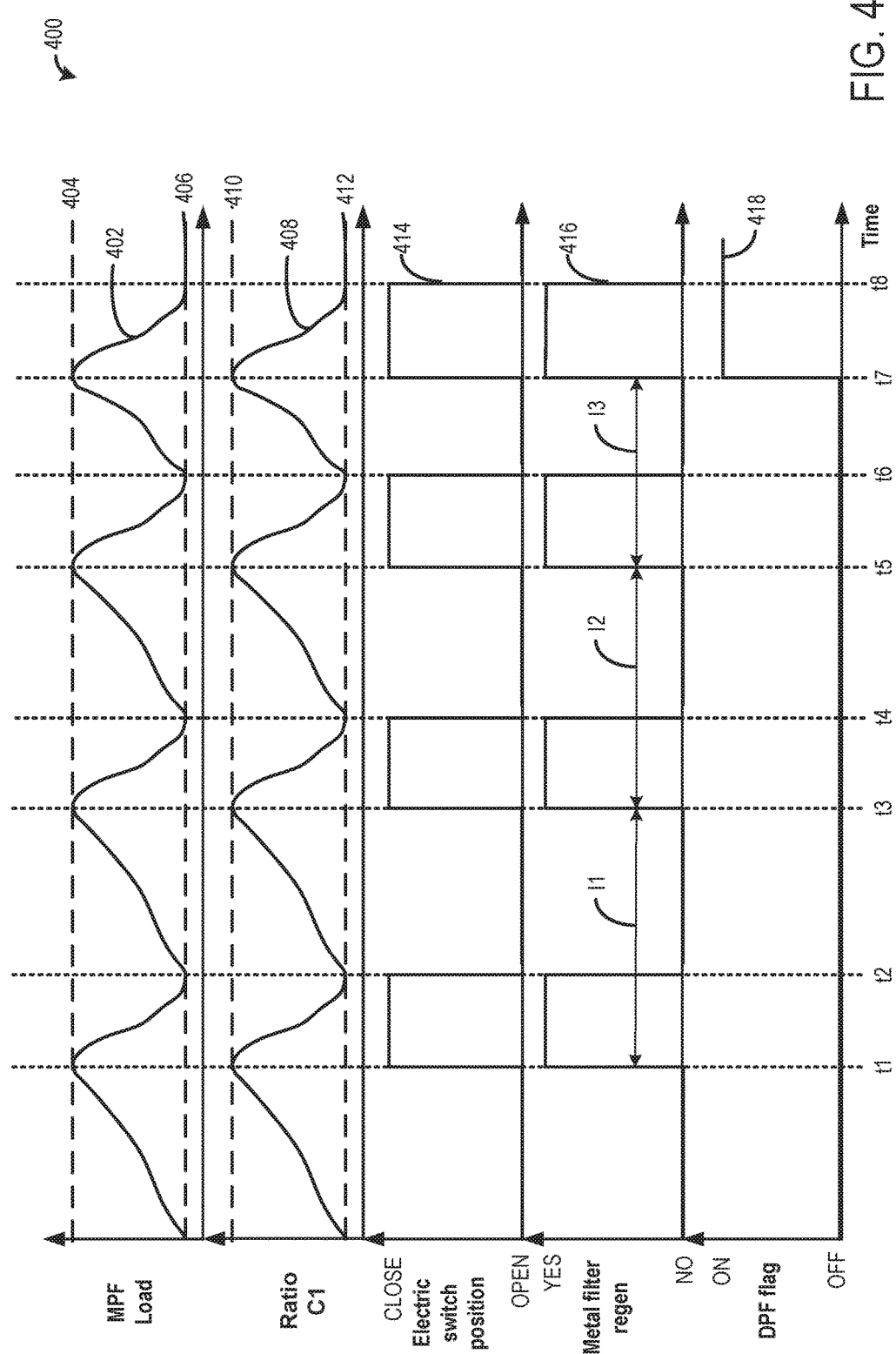
FIG. 4 shows an example of diagnosing a DPF based on the regeneration time of a metal filter coupled downstream of the DPF.
Figure 5:
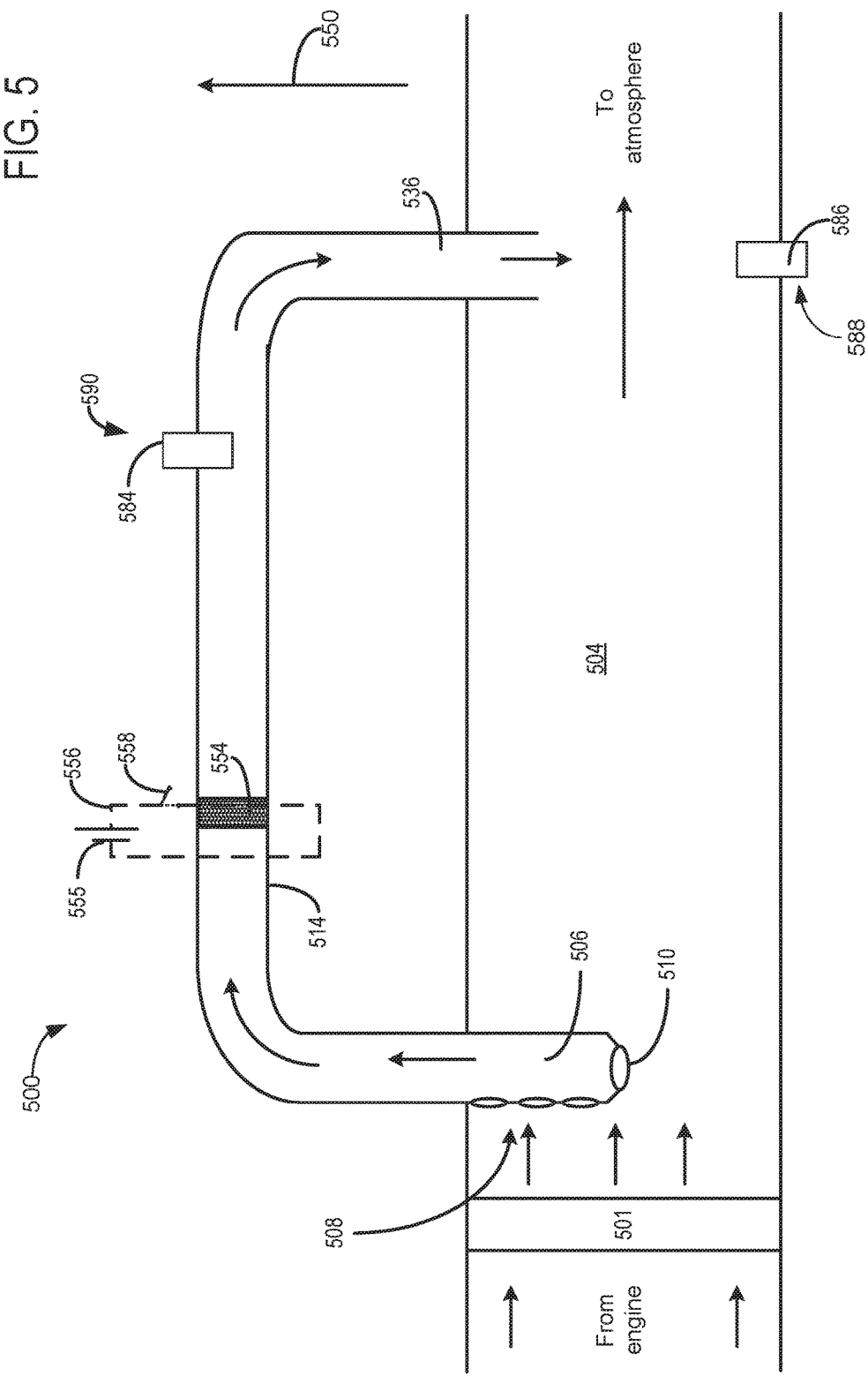
FIG. 5 shows an embodiment of a pressure difference based exhaust soot sensor assembly.

FIG. 4 shows an example operating sequence 400 illustrating an engine operating with a secondary soot sensor assembly (e.g., such as the secondary soot sensor assembly 200 shown in FIG. 2), and regenerating of a metal filter of the flow assembly. The method shows regenerating of the metal filter based on exhaust flow ratio between two venturi tubes of the assembly, and indicating degradation of an upstream particulate matter filter based on an interval between successive regenerations of the metal filter. The horizontal (x-axis) denotes time and the vertical markers t1-t8 identify significant times in the operation of the soot sensor assembly.

The first plot from the top shows soot deposition (line 402) on the metal particulate filter (MPF) over time (herein also referred to as the MPF load). The upper and the lower limit values are marked by dotted lines 404 and 406, respectively. The second plot (line 408) shows the variation in exhaust flow ratio (CI) between the first and second venturi tubes, as calculated using measurements from pressure sensors coupled between the motive inlet and the neck of the respective venturi tubes. The High and Low thresholds of the exhaust flow ratio between the venturi tubes is shown by the dotted lines 410 and 412, respectively. The third plot (line 414) shows the position of an electric switch of a circuit coupled to the metal filter. The fourth plot (line 416) indicates regeneration of the MPF and the bottom plot (line 418) represents a flag indicating whether the DPF is degraded or not.

Prior to time t1, as a portion of exhaust is diverted from downstream of a DPF into the exhaust bypass passage, a soot load on the metal filter in the downstream soot sensor assembly gradually increases (line 402). As the soot load on the metal filter increases, an exhaust flow through the second venturi in the bypass upstream of the metal filter decreases relative to exhaust flow through the first venturi in the exhaust passage. Consequently, as the soot load of the metal filter increases, a corresponding rise in the exhaust flow ratio between the two venturi tubes (line 408) is observed. That is, the rise in exhaust flow ratio is proportional to the increase in soot load on the metal filter. As such, prior to t1, while the exhaust flow ratio is below the upper threshold 410, the soot load is below the limit 404. During this time, a switch of the electric circuit of the soot assembly is held open and the metal filter does not regenerate. When the switch is in the open state, the circuit is open and there is no flow of current through it. In comparison, when the switch is in the closed state, the electric circuit coupled to the metal filter is complete and current flows through it. At t1, in response to the exhaust flow ratio reaching the upper threshold 410, the switch is closed, electric current starts flowing through the circuit and, regeneration of the metal filter is initiated. In addition, a timer is started upon initiation of the regeneration event.

Between t1 and t2, there is a decrease is exhaust flow ratio from which it can be inferred that the MPF load is decreasing. At t2, in response to exhaust flow ratio reaching lower threshold 412, it may be inferred that the soot load of the metal filter has been sufficiently reduced and regeneration of the filter is terminated by actuating the switch of the electric circuit to the open position. In this way, regeneration of the second filter is based on the ratio of flow rates through the first and second venturi tubes and includes initiating regeneration of the second filter when the ratio is higher than an upper threshold, and terminating regeneration of the second filter when the ratio is lower than a lower threshold.

After t2 and prior to t3, the exhaust flow ratio increases indicating an increase in metal filter soot load. During this time, the regeneration remains disabled with the switch in the open position and the DPF degradation flag is off. At t3, similar to t1, in response to the exhaust flow ratio reaching the upper threshold 410, the switch is closed, electric current flows through the circuit and regeneration of the metal filter is initiated. At this point the timer is stopped and the controller records the time interval elapsed between the onset of the current MF regeneration (at t3) and the onset of the previous metal filter regeneration (at t1). The time interval t1-t3 is denoted by I1.

If time interval I1 is less than a threshold time interval, then the DPF may be degraded. In particular, it may be determined that soot is leaking from the DPF onto the metal filter, requiring the metal filter to be regenerated more frequently. The threshold time interval may be based on an average time interval between successive regeneration events for a predefined number of regeneration events and/or for a predefined duration or distance of vehicle travel/engine operation and/or a predefined number of engine cycles. For example, the threshold time interval may be based on a time elapsed between completion of a regeneration event immediately preceding a first regeneration (such as the first regeneration at t1) and completion of the first regeneration, and the time interval between the first regeneration and a second regeneration (such as the second regeneration at t3) of the metal filter includes a time elapsed between completion of the first regeneration and completion of the second regeneration. In the current example, I1 is greater than the threshold and the degradation flag for the DPF is kept in OFF state. The timer is restarted at t3, upon initiation of the next regeneration event. In addition, due to no indication of degradation, regeneration of the DPF may be enabled when conditions are met, such as when a soot load of the DPF is determined to be sufficiently high.

Between t3 and t4, there is a decrease is exhaust flow ratio indicating that the MPF load decreases proportionally during this interval. At t4, as the exhaust flow ratio value reaches the lower threshold 412, it may be inferred that the soot load of the MPF has been sufficiently reduced. At this point the regeneration of MPF is complete and is terminated by actuating the switch of the electric circuit to the open position. The timer continues to record the time elapsed.

After t4 and prior to t5, the exhaust flow ratio increases until it reaches the upper threshold 410 at t5, triggering regeneration. It can be inferred that during this time period the soot load depositing on the MPF also increases. At t5, regeneration is initiated by actuating the switch to the closed position. At this point the timer records the time interval between the onset of the current metal filter (at t5) regeneration and that of the previous MPF regeneration (at t3).

The time interval t3-t5 is denoted by I2. The time interval I2 is compared to I1 and/or a threshold. If this time interval is less than the threshold time interval, then the DPF may be degraded. In the current example, I2 is greater than I1 and the degradation flag is kept in the OFF state. With the onset of the regeneration process at t5, the timer is restarted.

Between t5 and t6, regeneration of MPF continues and the exhaust flow ratio value decreases until it reaches the lower threshold 412, where it can be inferred that the soot level on the metal filter has decreased to the lower limit. At t6, regeneration is completed and the switch for the electric circuit is opened. During this time, the timer continues to record the time elapsed.

With the circuit open, the MPF regeneration is suspended and as seen for previous time cycles the exhaust flow ratio is seen to increase between t6 and t7 in response to the soot accumulation on the MPF. At t7, the exhaust flow ratio reaches the upper threshold 410 and in response, the switch is actuated to a closed position starting the regeneration process. The time interval between the current and the previous regeneration, I3 is recorded by the timer as the time difference between t5 and t7. The time elapsed is compared to the time interval for the last regeneration cycle I2. In the depicted example, current time interval I3 is determined to be shorter than I2, as well as I1, and/or a threshold (based at least on I2). Therefore, in response to the time interval for the current regeneration cycle being smaller than the time interval for a previous regeneration cycle (or a threshold duration), it may be indicated that the DPF is degraded by setting a flag at t7 (as shown at plot 418). The controller may then employ engine actuators of the engine system to reduce or limit an engine torque output in response to the degradation of the DPF. For example, in response to the indication of degradation, regeneration of the DPF may be disabled and engine operations may be adjusted by retarding spark timing and/or enriching the exhaust gas. However, regeneration of the metal filter may continue.

After t7 and prior to t8, the MPF regeneration process continues with the electric circuit closed. There is a reduction in the exhaust flow ratio indicating burning off soot deposited on the metal filter. However, at this stage, the DPF continues to be degraded and DPF regeneration continues to be discontinued. At t8, the metal filter regeneration is complete as the exhaust flow ratio reaches the lower threshold 412. After t8, soot continues to deposit on the MPF, however, the soot level may remain relatively low due to adjustments made in the engine by the controller in order to decrease overall exhaust soot output. In this way, DPF degeneration is diagnosed based on the regeneration time of a metal filter coupled downstream of the DPF.

The soot sensor assembly 200 illustrated in FIG. 2 has venturi along the exhaust pipe and the bypass passage. The first venturi and the second venturi of the soot sensor assembly 200 are each coupled to pressure sensors to assess flow rate ratio between the two venturis to determine filter degradation. FIG. 5 shows a schematic view of another embodiment of a secondary soot sensor assembly 500 based on pressure difference between two locations along an exhaust pipe to gauge filter degradation. Unlike the soot sensor assembly 200, the soot sensor assembly 500 illustrated in FIG. 5 has a uniform diameter exhaust pipe downstream of a DPF and a uniform diameter passage external to the exhaust pipe. Pressure sensors coupled directly to the exhaust pipe and to the passage external to the exhaust pipe can measure pressure and provide a pressure difference based system to diagnose filter degradation. By relying on the pressure differential at the two locations to determine filter degradation rather than the exhaust flow ratio, manufacture of the soot sensor assembly may be less complex, as the venturis in the system may be dispensed with. Further, the static pressure difference determination described below may be less computationally intensive and may be more accurate under certain conditions, such as low exhaust flow conditions.

In one example, the soot sensor assembly 500 may be an embodiment of the soot sensor assembly 90 of FIG. 1 and therefore may share common features and/or configurations as those already described for the soot sensor assembly 90. Secondary soot sensor assembly 500 may be fluidly coupled to an exhaust pipe 504. The exhaust pipe 504 may include a first filter 501. In one example, the first filter 501 may be a large diesel or gasoline particulate matter filter having a high soot capacity. The secondary soot sensor assembly 500 may be coupled to the exhaust pipe 504 downstream of the first filter 501. For example, the first filter 501 and the exhaust pipe 504 may be examples of particulate filter 72 and exhaust pipe 48 of FIG. 1.

Exhaust gas flowing from the engine passes through the first filter 501 and reaches the secondary soot sensor assembly 500 located further downstream along the exhaust pipe 504. Solid line arrows indicate a direction of the exhaust flow in the exhaust pipe 504 past the first filter 501. At least a portion of the exhaust gas flowing through the exhaust pipe 504 may be diverted into the secondary soot sensor assembly 500 via an inlet pipe 506. The inlet pipe leads to an exhaust bypass passage 514 external to the exhaust pipe 504. The bypass passage 514 ends in an outlet pipe 536 external to the exhaust pipe 504. The outlet pipe 536 directs the flow of exhaust gas back to the exhaust pipe 504 downstream of the inlet pipe 506. The bypass passage 514 between the inlet pipe 506 and the outlet pipe 536 may be straight and of uniform diameter.

A portion of each of the inlet pipe 506 and outlet pipe 536 is coupled internally to the exhaust pipe 504 and a remaining portion of each of the inlet pipe 506 and outlet pipe 536 is coupled externally to the exhaust pipe 504. The inlet pipe 506 extends though the exterior wall of the exhaust pipe 504 and into the interior of the exhaust pipe 504. In one example, the portion of inlet pipe 506 and outlet pipe 536 internal to exhaust pipe 504 is smaller than the remaining portion of inlet pipe 506 and outlet pipe 536 external to exhaust pipe 504, respectively. In the depicted example outlet pipe 536 has a shorter length relative to inlet pipe 506. In addition, the portion of outlet pipe 536 that dips internal to exhaust pipe 504 is smaller than the portion of inlet pipe 506 that dips internal to exhaust pipe 504.

The inlet pipe 506 comprises a plurality of perforations 508 on a side of the inlet pipe within the exhaust pipe 504 and proximate to the first filter 501. The perforations 508 face the first filter 501 and the direction of the oncoming exhaust gas flow. There are no perforations on the opposite side (wall) of the inlet pipe 506. As a result of this configuration, aggregated particulates and water droplets in the exhaust may impinge the inner face of the inlet pipe, and be released into the exhaust pipe, without affecting a sensitivity of the soot sensing assembly.

The centerline of the inlet pipe 506 is perpendicular to the centerline of the exhaust pipe 504 and the perforations 508 are completely situated inside the exhaust pipe 504. There may be more perforations configured on the inlet pipe 506 as compared to the outlet pipe 536. In one example, there may be no perforations on the outlet pipe 536, as depicted. A perforation 510 is located at the bottom of the inlet pipe 506 within the exhaust pipe 504. The perforation 510 is arranged perpendicular to the perforations 508 on inlet pipe 506. A diameter of the perforations on the inlet tube side wall may be adjusted to enable conglomerated particulates and water droplets in the exhaust gas to impinge on a side of the inlet pipe within the exhaust pipe and distal to the first filter 501, the conglomerated particulates being released from the inlet pipe into the exhaust pipe via a perforation 510 on a bottom of the inlet pipe. In this way, the conglomerated particulates and water droplets can then be released from the inlet pipe 506 into the exhaust pipe via a perforation 510 on a bottom of the inlet pipe reducing contamination of the exhaust bypass passage 514, thereby improving the accuracy of the secondary soot sensor assembly 500.

A part of the exhaust gas may flow from the exhaust pipe 504 into the inlet pipe 506 (shown by single solid arrow pointing upwards), and from the inlet pipe 506 into the exhaust bypass passage 514. The direction of flowing exhaust gas through the inlet pipe 506 and the outlet pipe 536 is substantially perpendicular to a direction of exhaust flow through the exhaust pipe 504. The portion of the inlet pipe 506 located outside of the exhaust pipe 504 has a lower temperature compared to the part of the inlet pipe 506 located inside the exhaust pipe 504. The temperature drop may cause the water vapor in the exhaust gas to condense on the surfaces of inlet pipe 506. The condensate may fall through the perforation 510 back into the exhaust pipe 504 thereby reducing the entry of water droplets into the secondary soot sensor assembly 500.

A first pressure sensor 586 may be coupled to the exhaust pipe 504. In one example, the first pressure sensor 586 may be at a first location 588 downstream of the first filter 501, downstream of the inlet pipe 506 coupling to the exhaust pipe 504, in proximity of the outlet pipe 536 coupling to the exhaust pipe 504. For example, first location 588 may be along a center axis of outlet pipe 536. First pressure sensor 586 may estimate static exhaust gas pressure at the first location 588. The first location 588 and the center of the exit of the bypass flow outlet pipe 536 are located within the same cross-section plane of the exhaust pipe 504, such that the outlet pipe 536 is fluidically coupled to the exhaust pipe and positioned to expel exhaust gas at the first location. Having the outlet pipe 536 fluidically opening near the first location, may direct exhaust bypass flow back into the exhaust pipe at the first location, generating more pressure at the first location than at other locations along the exhaust pipe, such as before the outlet pipe coupling to the exhaust pipe. The first pressure sensor 586 may measure the static pressure at the first location 588, downstream of the first filter 501 and downstream of the inlet 506 coupling to the exhaust pipe 504.

A metal particulate filter (MPF) 554 may be installed along the straight portion of the bypass passage 514, as illustrated in FIG. 5. The MPF 554 may be of lower porosity than the first filter 501, capturing the soot particulates that may pass through the first filter 501. The metal particulate filter (MPF) 554 is affixed across the straight portion of the bypass passage 514 upstream of a second pressure sensor 584. The MPF 554 faces perpendicular to the direction of exhaust flow into the bypass passage 514 such that the exhaust gas flows through the MPF 554. In one example, the MPF 554 is smaller compared to the first filter 501 and is located outside of the exhaust pipe 504 while first filter 501 is housed within exhaust pipe 504. The MPF 554 surface may be flat and/or disk-shaped, comprising of metal fibers. The metal filter effectively traps soot and particulate matter in its pores as exhaust gas flows from the inlet pipe 506 through the bypass passage 514 to outlet pipe 536. The portion of the exhaust gas exiting the first filter 501 and passing through the exhaust pipe 504 without entering the inlet pipe 506 passes through exhaust pipe 504 without flowing through any additional filters, at least until the exhaust passes the first pressure sensor 586.

Downstream of the MPF 554, along the straight portion of the bypass passage 514, the second pressure sensor 584 may be mounted to measure the static pressure at a second location 590. The second location 590 along the bypass passage 514 may be closer to the outlet pipe 536 than the inlet pipe 506. The second pressure sensor 584 may measure the static pressure due to exhaust flow along the bypass passage 514, downstream of the metal filter 554 at the second location 590.

The MPF 554 may be electrically coupled to a circuit 556 including a switch 558 and a source of electricity 555. In the depicted example, the source of electricity 555 includes a battery (or battery pack). The switch 558 may be alternated between an open position, indicated by a solid line, and a closed position, indicated by a dotted line. When the switch 558 is moved to the closed position, such as when MPF 554 regeneration conditions are met (for example, when the pressure difference drops below the threshold, indicating particulate material load on the MPF is above a threshold), the circuit 556 is completed and an electric current (drawn from the source of electricity 555) can pass through the metal filter 554 causing an increase in temperature at the filter. The heat generated may be used to regenerate the metal filter 554 by burning off soot captured on the metal filter surface over a period. At all times other than during metal filter 554 regeneration, the switch 558 may be left in the open position.

A pressure difference between the pressure of the exhaust flow sensed by the second pressure sensor 584 and the pressure of the exhaust flow sensed by the first pressure sensor 586 may be calculated via equation 3 depicted below.

$$\Delta P = P_0 - \overline{P}_0 \quad (3)$$

In equation 3, $\Delta P$ represents a pressure difference between pressure $P_0$ sensed by the second pressure sensor 584 and pressure $\overline{P}_0$ sensed by the first pressure sensor 586.

As long as the MPF is not completely plugged, exhaust may flow downstream of the MPF 554, towards the second pressure sensor 584, along the bypass passage 514. The pressure $P_0$ at the second location 590 is generally higher than the pressure at the first location 588 in the exhaust pipe 504. At any given location, pressure is inversely proportional to area of the location. As the area of the exhaust pipe at the first location may be larger than the area of the passage at the second location, pressure $P_0$ is generally greater than pressure $\overline{P}_0$, unless the MPF 554 is blocked. Hence, the pressure difference $\Delta P$ between the pressure $P_0$ at the second location 590 and the pressure $\overline{P}_0$ at the first location 588, calculated using the equation 3, is a positive number. As soot loading continues, the MPF 554 may be plugged in a way that minimal exhaust gas flows through the metal filter towards the downstream second pressure sensor 584 at the second location 590, generating a vacuum effect inside the bypass passage downstream of the metal filter. As a result, the static pressure $P_0$ at the second location 590 may be lower than the pressure $\overline{P}_0$ at the first location 588, and the pressure difference based on equation 3 may be zero or negative.

As soot accumulates in the metal filter over a period of time, exhaust backflow increases, which decreases the pressure $P_0$ at the second location 590. Consequently, the pressure difference $\Delta P$ decreases. When the pressure difference ΔP between the second location 590 and the first location 588 along the exhaust pipe reaches a first (lower) threshold, he MPF 554 may be regenerated by closing the switch in the 558 in circuit 556. Specifically, a controller may initiate regeneration of the MPF 554 when the pressure difference ΔP is equal to zero or negative, which may be indicative of a blocked MPF 554, and the controller may terminate regeneration of the MPF 554 when the pressure difference ΔP is a positive numerical value, indicative of higher pressure at the second location 590 compared to the pressure at the first location 588.

Thus, in response to the pressure difference between the pressure at the second location 590 and at the pressure at the first location 588, the engine controller may send a signal to actuate switch 558 of the electric circuit 556 to the closed position. On closing the switch 558, the electric circuit is completed and current flows through the metal filter 554 causing an increase in temperature. The heat generated starts burning away the soot deposit and regenerating the metal filter 554. As the soot deposit decreases, exhaust starts flowing through the metal filter toward the downstream second pressure sensor 584, increasing the pressure $P_O$ at the second location 590. The pressure difference ΔP starts increasing, approaching a positive value. When the pressure difference ΔP is at a pre-determined second (upper) threshold, it may be inferred that the metal filter 554 has been sufficiently regenerated and the controller sends a signal to actuate switch 558 of the circuit 556 to the open position, stopping further flow of current and filter regeneration.

When the DPF is degraded, more soot may travel downstream though the exhaust pipe 504 to the secondary soot sensor assembly 500. As a result, soot accumulates on the metal filter 554 at an increased rate, and regeneration of the metal filter 554 has to be carried out more frequently. Thus, by monitoring an interval between successive regenerations of the metal filter, degradation or leakage of the DPF may be determined.

In one embodiment, the soot sensor assembly 200 illustrated in FIG. 2 may be present in combination with the soot sensor assembly 500 illustrated in FIG. 5. The soot sensor assembly 200 with the first venturi 212 coupled to the pressure sensor 284 may additionally include a pressure sensor, such as the first pressure sensor 586 shown in FIG. 5, downstream of the first venturi 212 in the exhaust pipe. The passage external to the exhaust pipe with the second venturi 216 coupled to the pressure sensor 286 may include an additional pressure sensor (for example, the pressure sensor 584 illustrated in FIG. 5), downstream of the second venturi 216 and downstream of the MPF 224, along the straight portion of the passage external to the exhaust pipe. As described previously with reference to FIGS. 2-4, flow rate ratio between the first venturi and the second venturi may be used to assess filter degradation and for regulating filter regeneration. Additionally, a pressure difference system based on the difference in pressure measured by the pressure sensor downstream of the first venturi in the exhaust pipe and the pressure measured by the pressure sensor downstream of the second venturi and downstream of the MPF in the exhaust bypass passage may be used for assessing MPF and DPF degradation, as will be discussed with reference to FIGS. 6 and 7. In one example, the pressure difference system may act as a primary system for assessing MPF and DPF degradation and the flow rate ratio between the flow rate at the first venturi and the second venturi may act a secondary system for estimating filter degradation or vice versa. In case of a pressure sensor failure at one location, the back-up system may gauge filter degradation to ensure filter regeneration in a timely manner. Additionally, in some examples, the exhaust pressure difference determination described with respect to FIG. 5 may be more accurate during certain condition than the exhaust flow ratio determination described with respect to FIG. 2, such as during low exhaust gas flow conditions (e.g., idle engine operation). Thus, the controller may infer soot loading of the MPF using the pressure difference determination during some conditions while inferring soot loading of the MPF using the exhaust flow ratio determination during other conditions. Additionally or alternatively, the controller may infer a first level of soot loading from the pressure difference determination and infer a second level of soot loading from the exhaust flow ratio determination and determine an overall soot loading by averaging the first and second levels of soot loading.

FIG. 5 shows example configurations of the soot sensing assembly with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example.

Figure 6:
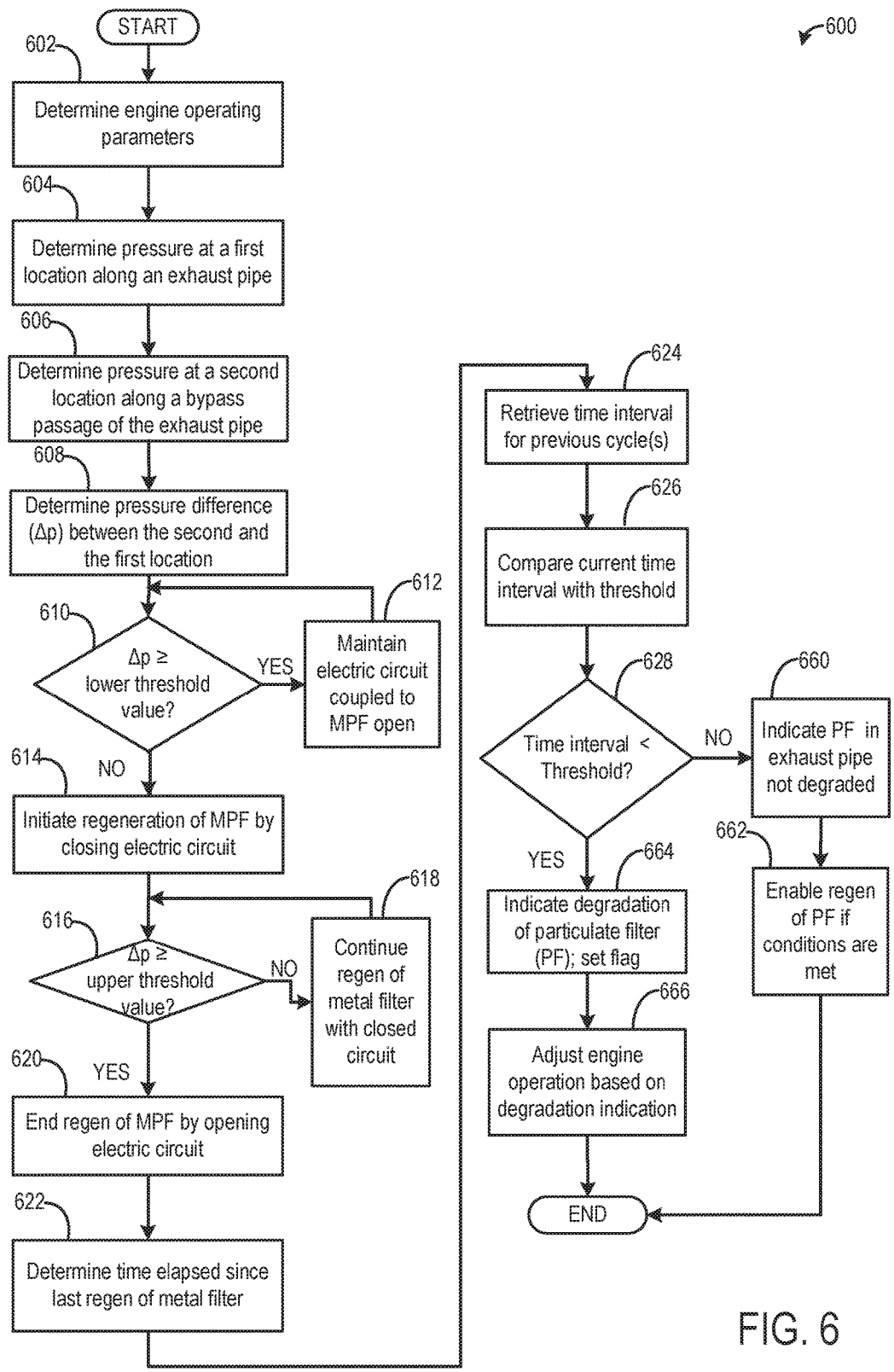
FIG. 6 shows a flow chart illustrating a method that may be implemented for diagnosing degradation of a DPF in the exhaust pipe based on pressure difference between two locations downstream of the DPF.
Figure 7:
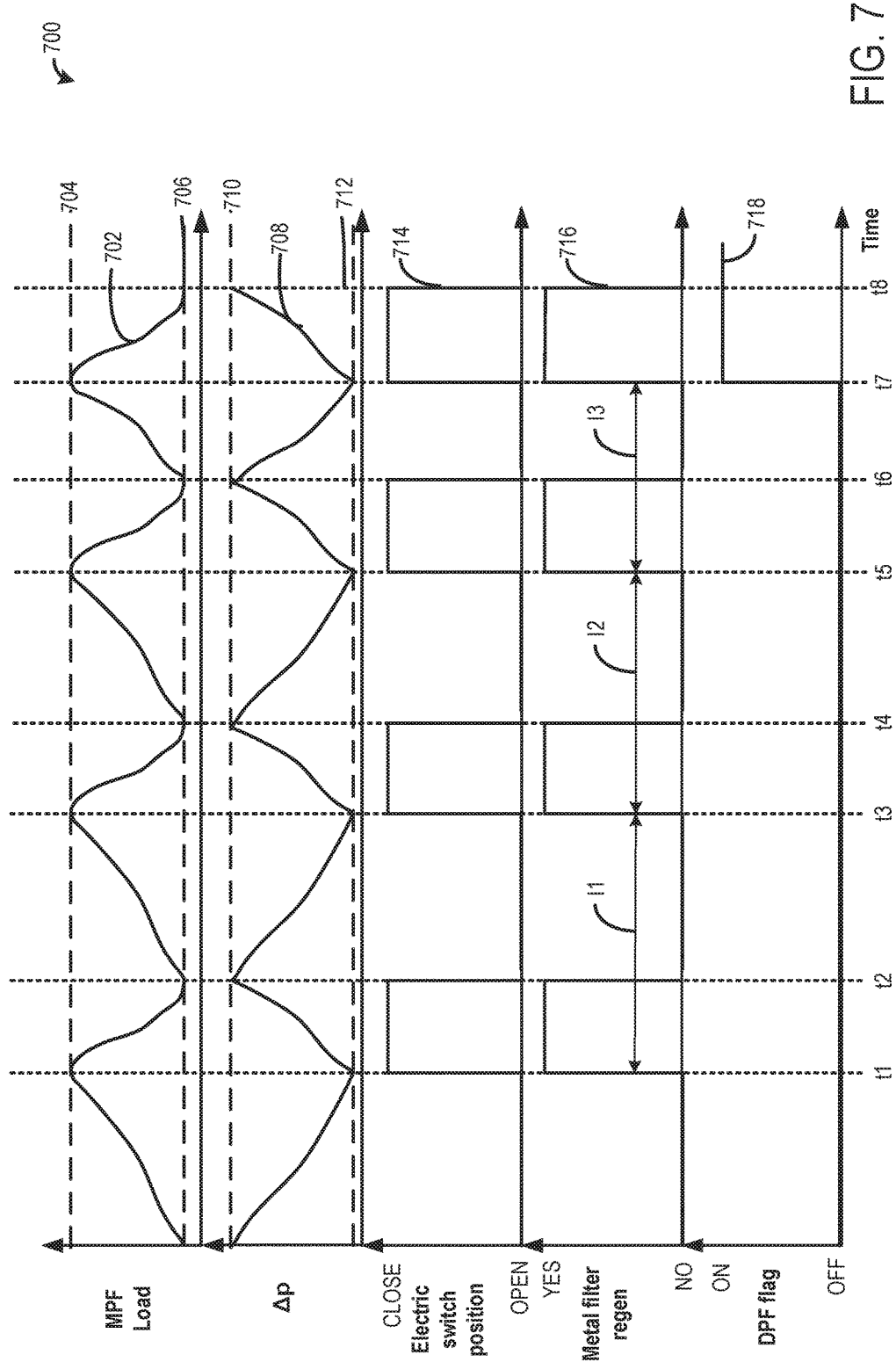
FIG. 7 shows an example of diagnosing a DPF based on the regeneration time of a metal filter coupled to the soot sensor assembly of FIG. 5.

FIG. 6 illustrates an example method 600 for diagnosing degradation of an exhaust particulate filter in an engine exhaust passage. In one example, method 600 may be used for diagnosing the degradation of the first filter 501 along the exhaust pipe 504 based on a regeneration frequency of and the second filter MPF 554 positioned in the bypass passage 514, as described above with reference to FIG. 5. Instructions for carrying out method 600 and the rest of the methods included herein may be executed by a controller based on instructions stored on a memory of the controller and in conjunction with signals received from sensors of the engine system, such as the first pressure sensor 586 and the second pressure sensor 584, described above with reference to FIG. 5. The controller may employ engine actuators of the engine system to adjust engine operation, such as actuator to reduce engine torque output, according to the methods described below.

At 602, the routine includes estimating and/or measuring current engine operating parameters. Parameters assessed may include, for example, engine load, engine speed, vehicle speed, manifold vacuum, throttle position, exhaust pressure, exhaust air/fuel ratio, etc. Parameters assessed may also include particulate material load downstream of a DPF, duration (or distance) elapsed since a last regeneration of the DPF, etc.

At 604, the routine determines the pressure at a first location along an exhaust pipe. The pressure may be estimated by a pressure sensor coupled to the exhaust pipe at the first location. In one example, the pressure may be determined at the first location 588 along the exhaust pipe 504 by the pressure sensor 586, as described above with reference to FIG. 5

At 606, the routine determines the pressure at a second location downstream of a filter along a bypass passage of an exhaust pipe. In one example, pressure may be determined by the second pressure sensor 584 at the second location 590 downstream of the MPF 554, as illustrated in FIG. 5.

At 608, the routine includes determining a pressure difference ΔP between the pressure at the second location and the pressure at the first location. The pressure difference may be estimated by using equation 3, as described above with reference to FIG. 5. As soot deposits on the metal filter located on the exhaust bypass passage, exhaust flow through the MPF towards the downstream pressure sensor in the bypass passage may decrease, and thus the pressure difference between the second location and the first location may decrease, approaching zero or negative values.

At 610, the routine includes determining if the pressure difference ΔP is greater than or equal to a pre-determined lower threshold, wherein the lower threshold may be zero or a negative number. Herein, the lower threshold is a threshold that indicates the metal filter has reached a soot-loading capacity and below which the metal filter in the exhaust bypass passage may have to be regenerated. The lower threshold may be based on engine operating conditions, such as engine load and/or the soot load of the first filter. If the pressure difference ΔP is higher than the lower threshold, the routine proceeds to 612 to maintain the switch of the electric circuit in the open position, and the routine loops back to 610 to continue monitoring the pressure difference between the two locations. When the switch of the electric circuit coupled to the second metal filter in the bypass passage is in the open position, no current flows through the circuit, and regeneration of the metal filter is not initiated.

If the pressure difference ΔP between the second location and the first location is not greater than the lower threshold, the routine proceeds to 614 where the controller (such as controller 12 of FIG. 1) sends a signal to actuate the switch of the electric circuit coupled to the metal filter to a closed position in order to complete the circuit. On circuit completion, electricity (that is, an electric current) flows through the metal filter and regeneration of the filter starts. In this way, regeneration of the second metal filter is carried out responsive to pressure at the second location being less than the pressure at the first location along the exhaust pipe. As described above, by closing the circuit, the metal filter is heated electrically, effectively burning soot deposited on the filter. The regenerating of the metal filter is continued with the switch of the electric circuit closed and by flowing electricity (current) through the metal filter until the pressure difference between the second location and the first location is higher than the higher threshold. Thus, the switch may remain in the closed position until regeneration of the second metal filter is completed.

At 616, the routine includes determining if the pressure difference ΔP between the pressure at the second location and the pressure at the first location is equal to or greater than a pre-determined upper threshold. The upper threshold, like the lower threshold, may be adjusted based on engine operating conditions, such as a soot load of the first filter, as well as the porosity of the second smaller metal filter. If the pressure difference ΔP is lower than the upper threshold, the routine moves to 618 where the controller continues with the regeneration process by maintaining the switch, and consequently the circuit, closed.

Upon confirming that pressure difference is equal to or higher than the upper threshold, at 620, the regeneration process may be stopped. Therein, the controller may send a signal to actuate the switch of the electric circuit coupled to the metal filter to an open position. As a result, current stops flowing through the circuit, terminating the regeneration. In this way, regenerating the metal filter includes closing a switch of the electric circuit and flowing electricity through the metal filter until the pressure difference between the second location and the second location is above the lower threshold.

At 622, the routine includes determining a time elapsed since a previous regeneration of the metal filter. As such, this corresponds to a time interval between the previous regeneration and a current regeneration of the metal filter. Alternately, this may be determined as a time elapsed since a last opening of the switch. The interval is measured from initiation of a first regeneration event of the metal filter to initiation of a second, immediately subsequent regeneration event of the metal filter, with no regenerations in between. In one example, a timer may be started when a regeneration of the filter is completed (such as when the switch is opened at 620), and the timer may be stopped when a subsequent regeneration of the filter is completed (such as when the switch is opened during a subsequent iteration of method 600). The time intervals between successive regenerations may be stored in the memory of the controller.

At 624, the routine includes retrieving the time interval for the previous cycle. In an alternate example, an average duration between successive regeneration events of the metal filter over a duration or distance of vehicle operation, or a threshold number of engine cycles may be determined. The number of previous cycles used to determine the average time interval may be varied.

At 626, the routine includes comparing the current time interval (determined at 622) to a threshold time interval, the threshold including the time interval for the previous cycle (or the retrieved average time interval) as determined at 624. The interval is measured from initiation of a first regeneration event of the metal filter to initiation of a second, immediately subsequent regeneration event of the metal filter. During standard engine operation and when the DPF operates without degradation, the amount of soot deposited on the metal filter after each regeneration cycle may be comparable, resulting in intermittent regenerations with a symmetric periodicity. However, with age and durability issues, when the DPF becomes degraded, an increasing amount of soot may escape uncaptured by the DPF, and travel downstream through the exhaust pipe. This increased soot load may partly accumulate on the metal filter and as a result, the metal filter may have to be regenerated (cleaned) more frequently.

At 628, the routine determines if the current time interval is less than the threshold. If the time interval is not less than the threshold, it may be indicated at 660 that the DPF is not degraded. At 662, in response to the time interval being greater than the threshold time interval, regeneration of the particulate filter in the engine exhaust conduit may be initiated when particulate filter regeneration conditions are met. The regeneration conditions may include the particulate material load on the main engine exhaust conduit particulate filter being above a threshold (which may be determined based on a number of MPF regenerations performed since a previous particulate filter regeneration), duration (or distance) elapsed since a last regeneration of the filter, etc. The regeneration is initiated via one or more of a retarding spark and decreasing an air/fuel ratio.

If the time interval is less than the threshold, the routine proceeds to 664 to indicate degradation of the DPF. For example, it may be indicated that there is a leak, hole, crack, or other damage to the DPF. The indicating may include setting a flag or a diagnostic code, or activating a malfunction indicator lamp in order to notify the vehicle operator that the DPF is degraded. In this way, degradation of a DPF is indicated responsive to the interval between successive regenerations of a metal filter, located downstream of the DPF, being lower than a threshold duration.

At 666, in response to the indication of degradation, the controller may adjust the operation of one or more engine actuators to adjust engine operation. As one example, in response to the indication of degradation, the controller may limit an engine speed or load (e.g., by reducing an opening of an intake throttle), limit an engine torque output, and/or reduce boost pressure (e.g., opening a wastegate coupled to an exhaust turbine or a bypass valve coupled to an intake compressor).

In this way, engine operation may be adjusted based on degradation of a particulate filter positioned in an engine exhaust conduit, the degradation determined based on a time interval between a first regeneration and a second regeneration of a metal filter positioned in an exhaust bypass, the exhaust bypass external to the exhaust passage. The first and second regeneration are based on pressure difference between the pressure at the second location and the pressure at first location.

FIG. 7 shows an example operating sequence 700 illustrating an engine operating with a pressure difference-based secondary soot sensor assembly, and regenerating a metal particulate filter (MPF) of the secondary soot sensor assembly and diagnosing a diesel particulate filter (DPF) (for example, the secondary soot sensor assembly 500 with the first filter 501 and the second metal filter 554 illustrated in FIG. 5). The operating sequence shows regenerating of the metal filter based on a pressure difference between two locations along an exhaust pipe, and indicating degradation of an upstream diesel particulate filter (DPF) based on an interval between successive regenerations of the metal filter. The horizontal (x-axis) denotes time and the vertical markers t1-t8 identify significant times in the operation of the soot sensor assembly.

The first plot from the top shows soot deposition (line 702) on the metal particulate filter (MPF) over time (herein also referred to as the MPF load). The MPF load upper threshold and the MPF load lower threshold values marked by dotted lines 704 and 706, respectively. The second plot (line 708) shows the pressure difference ($\Delta P$) between the second location and the first location, as calculated using measurements from pressure sensors coupled to the bypass passage downstream of the MPF and the exhaust pipe, respectively. The upper and lower thresholds of the pressure difference is shown by the dotted lines 710 and 712, respectively. The third plot (line 714) shows the position of an electric switch of a circuit coupled to the metal filter. The fourth plot (line 716) indicates regeneration of the MPF and the bottom plot (line 718) represents a flag indicating whether the DPF is degraded.

Prior to time t1, as a portion of exhaust is diverted from downstream of a DPF into the exhaust bypass passage, a soot load on the metal filter in the downstream soot sensor assembly gradually increases (line 702). As the soot load on the metal filter increases, pressure measured by the pressure sensor downstream of the MPF, coupled to the bypass passage the exhaust flow pipe, decreases relative to the pressure measured by the pressure sensor at the first location along the exhaust pipe. Consequently, as the soot load of the metal filter increases, a corresponding decrease in the pressure difference $\Delta P$ between the pressures at the two locations is observed. The decrease in the pressure difference $\Delta P$ is proportional to the increase in soot load on the metal filter.

As such, prior to t1, while the pressure difference $\Delta P$ is above the lower threshold 712, the soot load is below the MPF load upper threshold 704. During this time, a switch of the electric circuit of the soot assembly is held open and the metal filter does not regenerate. When the switch is in the open state, the circuit is open and there is no flow of current through it. In comparison, when the switch is in the closed state, the electric circuit coupled to the metal filter is complete and current flows through it. At t1, in response to the pressure difference $\Delta P$ reaching the lower threshold 712, the switch is closed, electric current starts flowing through the circuit and regeneration of the metal filter is initiated. In addition, a timer is started upon initiation of the regeneration event.

Between t1 and t2, there is an increase in the pressure difference $\Delta P$ from which it can be inferred that the MPF load is decreasing. At t2, in response to the pressure difference $\Delta P$ reaching the upper threshold 710, it may be inferred that the soot load of the metal filter has been sufficiently reduced and regeneration of the filter is terminated by actuating the switch of the electric circuit to the open position. In this way, regeneration of the MPF is based on the pressure difference between the second location and the first location along the exhaust pipe, and includes initiating regeneration of the metal filter when pressure difference is equal to or less than the lower threshold 712, and terminating regeneration of the MPF when the pressure difference $\Delta P$ is at the upper threshold 710.

After t2 and prior to t3, the pressure difference $\Delta P$ decreases indicating an increase in metal filter soot load. During this time, the regeneration remains disabled with the switch in the open position and the DPF degradation flag is off. At t3, similar to t1, in response to the exhaust pressure difference reaching the upper threshold 710, the switch is closed, electric current flows through the circuit and regeneration of the metal filter is initiated. At this point, the timer is stopped and the controller records the time interval elapsed between the onset of the current MPF regeneration (at t3) and the onset of the previous metal filter regeneration (at t1). The time interval t1-t3 is denoted by I1.

If time interval I1 is less than a threshold time interval, then the DPF may be degraded. In particular, it may be determined that soot is leaking from the DPF onto the metal filter, requiring the metal filter to be regenerated more frequently. The threshold time interval may be based on an average time interval between successive regeneration events for a predefined number of regeneration events and/or for a predefined duration or distance of vehicle travel/engine operation and/or a predefined number of engine cycles. For example, the threshold time interval may be based on a time elapsed between completion of a regeneration event immediately preceding a first regeneration (such as the first regeneration at t1) and completion of the first regeneration, and the time interval between the first regeneration and a second regeneration (such as the second regeneration at t3) of the metal filter includes a time elapsed between completion of the first regeneration and completion of the second regeneration. In the current example, I1 is greater than the threshold and the degradation flag for the DPF is kept in OFF state. The timer is restarted at t3, upon initiation of the next regeneration event. In addition, due to no indication of degradation, regeneration of the DPF may be enabled when conditions are met, such as when a soot load of the DPF is determined to be sufficiently high.

Between t3 and t4, there is an increase in pressure difference $\Delta P$ indicating that the MPF load decreases proportionally during this interval. At t4, as the pressure difference $\Delta P$ reaches the upper threshold 710, it may be inferred that the soot load of the MPF has been sufficiently reduced. At this point, the regeneration of MPF is complete and is terminated by actuating the switch of the electric circuit to the open position. The timer continues to record the time elapsed.

After t4 and prior to t5, the pressure difference ΔP decreases until it reaches the lower threshold 712 at t5, triggering regeneration. It can be inferred that during this period the soot load depositing on the MPF also increases. At t5, regeneration is initiated by actuating the switch to the closed position. At this point the timer records the time interval between the onset of the current metal filter (at t5) regeneration and that of the previous MPF regeneration (at t3). The time interval t3-t5 is denoted by I2. The time interval I2 is compared to I1 and/or a threshold. If this time interval is less than the threshold time interval, then the DPF may be degraded. In the current example, I2 is greater than the threshold and the degradation flag is kept in the OFF state. With the onset of the regeneration process at t5, the timer is restarted.

Between t5 and t6, regeneration of MPF continues and the pressure difference ΔP value increases until it reaches the upper threshold 710, where it can be inferred that the soot level on the metal filter has decreased to the MPF load lower threshold. At t6, regeneration is completed and the switch for the electric circuit is opened. During this time, the timer continues to record the time elapsed.

With the circuit open, the MPF regeneration is suspended and as seen for previous time cycles the exhaust flow ratio is seen to increase between t6 and t7 in response to the soot accumulation on the MPF. At t7, the pressure difference ΔP reaches the lower threshold 712 and in response the switch is actuated to a closed position starting the regeneration process. The time interval between the current and the previous regeneration, I3 is recorded by the timer as the time difference between t5 and t7. The time elapsed is compared to the time interval for the last regeneration cycle I2. In the depicted example, current time interval I3 is determined to be shorter than I2, as well as I1, and/or a threshold (based at least on I2). Therefore, in response to the time interval for the current regeneration cycle being smaller than the time interval for a previous regeneration cycle (or a threshold duration), it may be indicated that the DPF is degraded by setting a flag at t7 (as shown at plot 718). The controller may then employ engine actuators of the engine system to reduce or limit an engine torque output in response to the degradation of the DPF. For example, in response to the indication of degradation, regeneration of the DPF may be disabled and engine operations may be adjusted by retarding spark timing and/or enriching the exhaust gas. However, regeneration of the metal filter may continue.

After t7 and prior to t8, the MPF regeneration process continues with the electric circuit closed. There is an increase in the pressure difference ΔP, indicating burning off soot deposited on the metal filter. However, at this stage, the DPF continues to be degraded and DPF regeneration continues to be discontinued. At t8, the metal filter regeneration is complete as the pressure difference ΔP reaches the upper threshold 710. After t8, soot continues to deposit on the MPF, however, the soot level may remain relatively low due to adjustments made in the engine by the controller in order to decrease overall exhaust soot output. In this way, DPF degeneration is diagnosed based on the regeneration time of a metal filter coupled downstream of the DPF One example method for DPF leakage detection comprises flowing exhaust gas from downstream of a first filter into each of a first venturi coupled inside an exhaust pipe and a second venturi coupled in a passage external to the exhaust pipe, the passage including a second filter coupled to an electric circuit; and indicating degradation of the first filter based on an interval between successive regenerations of the second filter. The preceding example further comprises in response to the indication, limiting an engine speed or load. In any or all of the preceding examples, additionally or optionally, the interval is measured from initiation of a first regeneration event of the second filter to initiation of a second, immediately subsequent regeneration event of the second filter. Any or all of the preceding examples additionally or optionally comprise regenerating the second filter responsive to a ratio of flow rates through the first and second venturi being higher than an upper threshold. In any or all of the preceding examples, additionally or optionally, the first venturi is larger than the second venturi, and wherein the ratio of flow rates through the first and second venturi is based on a first pressure at a motive inlet of the first venturi relative to a second pressure at the motive inlet of the second venturi. In any or all of the preceding examples, the first pressure is additionally or optionally estimated by a first pressure sensor coupled to the motive inlet of the first venturi, and the second pressure is estimated by a second pressure sensor coupled to the motive inlet of the second venturi. In any or all of the preceding examples, regenerating the second filter additionally or optionally includes closing a switch of the electric circuit and flowing electricity through the second filter until ratio of flow rates through the first and second venturi is lower than a lower threshold. In any or all of the preceding examples, additionally or optionally, the first filter is a larger diesel or gasoline particulate matter filter having a higher soot capacity, and the second filter is a smaller metal filter having a lower soot capacity, and wherein the indicating includes indicating the first filter is leaking by setting a diagnostic code. In any or all of the preceding examples, additionally or optionally, the second filter is coupled downstream of the second venturi, and flowing exhaust into the second venturi includes flowing exhaust gas from the exhaust pipe into an inlet pipe, and from the inlet pipe into the passage, the inlet pipe converging with the passage at a location external to the exhaust pipe, and from the passage into the exhaust pipe via an outlet pipe, the passage converging into the outlet pipe at a location downstream of the second filter and external to the exhaust pipe. In any or all of the preceding examples, additionally or optionally, a direction of flowing exhaust gas through the inlet pipe and the outlet pipe is substantially perpendicular to a direction of exhaust flow through each of the exhaust pipe, and the first and second venturi.

In another example, an engine exhaust system comprises: an exhaust pipe including a first venturi tube coupled downstream of a first particulate filter; a soot detection system including an inlet pipe and an outlet pipe coupled to the exhaust pipe, downstream of the first particulate filter, the inlet pipe merging into a second venturi tube external to the exhaust pipe, the outlet pipe merging out of the second venturi tube external to the exhaust pipe; a second particulate filter coupled between a motive outlet of the second venturi tube and the outlet pipe, the second particulate filter coupled to a source of electricity via a switch; one or more sensors for estimating a flow rate through each of the first and second venturi tubes; and a controller. The controller may be configured with computer readable instructions stored on non-transitory memory for: flowing a first portion of exhaust gas from downstream of the first filter through the first venturi tube; flowing a remaining portion of exhaust gas through the second venturi tube; regenerating the second filter based on a ratio of flow rates through the first and second venturi tubes; and adjusting engine operation based on a time elapsed between successive regenerations of the second filter. In the preceding example system, additionally or optionally, the inlet pipe comprises a plurality of perforations on a side of the inlet pipe within the exhaust pipe and proximate to the first filter, a diameter of the perforations adjusted to enable conglomerated particulates to impinge on a side of the inlet pipe within the exhaust pipe and distal to the first filter, the conglomerated particulates released from the inlet pipe into the exhaust pipe via a perforation on a bottom of the inlet pipe. In any or all of the preceding examples, additionally or optionally, the one or more sensors include a first pressure sensor coupled between a motive inlet and neck of the first venturi tube for estimating the flow rate through the first venturi tube, and a second pressure sensor coupled between the motive inlet and neck of the second venturi tube for estimating the flow rate through the second venturi tube. In any or all of the preceding examples, additionally or optionally, the first venturi tube is a larger venturi tube with a higher flow rate, and the second venturi tube is a smaller venturi tube with a lower flow rate. In any or all of the preceding examples, additionally or optionally, regenerating the second filter based on the ratio of flow rates through the first and second venturi tubes includes initiating regeneration of the second filter when the ratio is higher than an upper threshold, and terminating regeneration of the second filter when the ratio is lower than a lower threshold. In any or all of the preceding examples, additionally or optionally, adjusting engine operation based on a time elapsed between successive regenerations of the second filter includes regenerating the first filter when the time elapsed is higher than a threshold interval by retarding spark timing or enriching the exhaust gas, and indicating degradation of the first filter when the time elapsed is lower than the threshold interval, regeneration of the first filter discontinued responsive to the indication of degradation.

Another example method for an engine exhaust comprises adjusting engine operation based on degradation of a particulate filter positioned in an engine exhaust conduit, upstream of a first venturi, the degradation determined based on a time interval between a first regeneration and a second regeneration of a metal filter positioned downstream of a second venturi in an exhaust bypass, the exhaust bypass coupled across the first venturi and external to the exhaust passage, the first and second regeneration based on a ratio of flow rates across the first and second venturi. The preceding example additionally or optionally further includes: during a first condition, in response to the time interval being greater than a threshold time interval, regenerating the particulate filter in the engine exhaust conduit when particulate filter regeneration conditions are met via one or more of a retarding spark and decreasing an air/fuel ratio; and during a second condition, in response to the time interval being less than the threshold time interval, indicating to an operator degradation of the particulate filter and adjusting an engine actuator to reduce engine torque output. In any or all of the preceding examples, he threshold time interval may be additionally or optionally based on a time elapsed between completion of a regeneration event immediately preceding the first regeneration and completion of the first regeneration, wherein the time interval between the first regeneration and the second regeneration of a metal filter includes a time elapsed between completion of the first regeneration and completion of the second regeneration. In any or all of the preceding examples, additionally or optionally, the first and second regeneration based on the ratio includes regenerating the second filter when the ratio of the flow rate through the first venturi relative to the flow rate through the second venturi is higher than an upper threshold, the flow rate through the first venturi based on an estimated pressure upstream of a neck of the first venturi, the flow rate through the second venturi based on an estimated pressure upstream of the neck of the second venturi, and maintaining the regenerating until the ratio is lower than a lower threshold.

In this way, by diverting a portion of exhaust gas from an exhaust pipe to a secondary soot sensor assembly with a metal filter, located downstream of a diesel particulate filter, degradation of a particulate filter can be detected accurately. By flowing exhaust through each of a venturi tube in the primary exhaust pipe and a venturi tube in an exhaust bypass with the metal filter, the flow rates through the venturis may be advantageously leveraged to diagnose an upstream particulate filter. By relying on an exhaust flow ratio between the two venturi tubes to estimate the loading of the metal filter, the requirement for multiple pressure or flow sensors is reduced without reducing an accuracy of soothe diagnostics. By trapping aggregated particulates and water droplets in an inlet pipe of the soot sensor assembly, and redirecting them to the exhaust tailpipe, corruption of sensor results due to impingement of aggregates and water droplets is reduced. By rendering the soot sensor more accurate and reliable, emissions compliance is increased.

Another example method includes, flowing exhaust gas from downstream of a first filter towards each of a first pressure sensor coupled at a first location in an exhaust pipe and a second pressure sensor coupled at a second location in a passage external to the exhaust pipe, the passage including a second filter coupled to an electric circuit; and indicating degradation of the first filter based on an interval between successive regenerations of the second filter. In a first example of the method, further comprising, measuring a first pressure at the first location by the first pressure sensor coupled to the exhaust pipe, and measuring a second pressure at the second location by the second pressure sensor coupled downstream of the second filter in the passage external to the exhaust pipe. A second example of the method optionally includes the first example and further includes regenerating the second filter responsive to a pressure difference between the second pressure and the first pressure being lower than a lower threshold. A third example of the method optionally includes one or more of the first and second examples, and further includes regenerating the second filter by closing a switch of the electric circuit and flowing electricity through the second filter until the pressure difference between the second pressure and the first pressure is higher than an upper threshold. A fourth example of the method optionally includes one or more of the first through third examples, and further includes, in response to the indication, limiting an engine speed or load. A fifth example of the method optionally includes one or more of the first through fourth examples, and further includes, wherein the indicating includes indicating degradation responsive to the interval between successive regenerations of the second filter being lower than a threshold duration. A sixth example of the method optionally includes one or more of the first through fifth examples, and further includes, wherein the interval is measured from initiation of a first regeneration event of the second filter to initiation of a second, immediately subsequent regeneration event of the second filter. A seventh example of the method optionally includes one or more of the first through sixth examples, and further includes wherein the first filter is a diesel or gasoline particulate matter filter having a first, higher soot capacity, and wherein the second filter is a metal filter having a second, lower soot capacity, and wherein the indicating includes indicating the first filter is leaking by setting a diagnostic code. An eighth example of the method optionally includes one or more of the first through seventh examples, and further includes wherein the second filter is coupled upstream of the second pressure sensor, and wherein flowing exhaust towards the second pressure sensor includes flowing exhaust gas from the exhaust pipe into an inlet pipe, from the inlet pipe into the passage, the inlet pipe converging with the passage at a location external to the exhaust pipe, and from the passage into the exhaust pipe via an outlet pipe, the passage converging into the outlet pipe at a location downstream of the second pressure sensor and external to the exhaust pipe. A ninth example of the method optionally includes one or more of the first through eighth examples, and further includes wherein a direction of flowing exhaust gas through the inlet pipe and the outlet pipe is substantially perpendicular to a direction of exhaust flow through each of the exhaust pipe and the passage.

An example engine exhaust system, comprising an exhaust pipe including a first particulate filter, a soot detection system including an inlet pipe and an outlet pipe coupled to the exhaust pipe, downstream of the first particulate filter, the inlet pipe merging into a passage external to the exhaust pipe, the outlet pipe merging out of the passage external to the exhaust pipe, a second particulate filter coupled to the passage between the inlet pipe and the outlet pipe, the second particulate filter coupled to a source of electricity via a switch, a first pressure sensor at a first location in the exhaust pipe, a second pressure sensor at a second location in the passage external to the exhaust pipe, and a controller with computer readable instructions stored on non-transitory memory for flowing a first portion of exhaust gas from downstream of the first filter towards the first pressure sensor, flowing a remaining portion of exhaust gas towards the second pressure sensor, regenerating the second filter based on output from first and the second pressure sensors; and adjusting engine operation based on a time elapsed between successive regenerations of the second filter. A first example of the system includes, wherein the inlet pipe comprises a plurality of perforations on a side of the inlet pipe within the exhaust pipe and proximate to the first filter, a diameter of the perforations sized to enable conglomerated particulates to impinge on a side of the inlet pipe within the exhaust pipe and distal to the first filter, the conglomerated particulates released from the inlet pipe into the exhaust pipe via a perforation on a bottom of the inlet pipe. A second example of the system optionally includes the first example and further includes, wherein the first location is downstream of the first filter in the exhaust pipe and the second location is downstream of the second filter in the passage external to the exhaust pipe. A third example of the system optionally includes the first through second examples and further includes, wherein regenerating the second filter based on the pressure difference between the first location and the second location includes initiating regeneration of the second filter when the pressure difference is lower than a lower threshold, and terminating regeneration of the second filter when the pressure difference is higher than a upper threshold. A fourth example of the system optionally includes the first through third examples and further includes, wherein adjusting engine operation based on a time elapsed between successive regenerations of the second filter includes regenerating the first filter when the time elapsed is higher than a threshold interval by retarding spark timing or enriching the exhaust gas, and indicating degradation of the first filter when the time elapsed is lower than the threshold interval, further comprising ceasing regeneration of the first filter responsive to the indication of degradation.

Another example method includes, adjusting engine operation based on degradation of a particulate filter positioned in an engine exhaust conduit, upstream of a first pressure sensor, the degradation determined based on a time interval between a first regeneration and a second regeneration of a metal filter positioned upstream of a second pressure sensor in an exhaust bypass, the exhaust bypass external to the exhaust passage, the first regeneration and the second regeneration each performed based on a pressure difference between a pressure measured by the second pressure sensor and a pressure measured by the first pressure sensor. A first example of the method optionally includes, in response to the time interval being greater than a threshold time interval, regenerating the particulate filter in the engine exhaust conduit when particulate filter regeneration conditions are met via one or more of a retarding spark and decreasing an air/fuel ratio, and in response to the time interval being less than the threshold time interval, indicating to an operator degradation of the particulate filter and adjusting an engine actuator to reduce engine torque output, wherein the threshold time interval is based on a time elapsed between completion of a regeneration event immediately preceding the first regeneration and completion of the first regeneration, and wherein the time interval between the first regeneration and the second regeneration of the metal filter includes a time elapsed between completion of the first regeneration and completion of the second regeneration. A second example of the method optionally includes the first example and further includes, wherein performing each of the first regeneration and the second regeneration based on the pressure difference includes regenerating the second filter when the pressure difference between the second location and the first location is lower than a lower threshold, and maintaining the regenerating until the pressure difference is higher than an upper threshold.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
    flowing exhaust from downstream of a first filter towards each of a first pressure sensor coupled at a first location in an exhaust pipe and a second pressure sensor coupled at a second location in a passage external to the exhaust pipe, the passage including a second filter coupled to an electric circuit; and indicating degradation of the first filter based on an interval between successive regenerations of the second filter.

2. The method of claim 1, further comprising, measuring a first pressure at the first location by the first pressure sensor coupled to the exhaust pipe, and measuring a second pressure at the second location by the second pressure sensor coupled downstream of the second filter in the passage external to the exhaust pipe.

3. The method of claim 2, further comprising, regenerating the second filter responsive to a pressure difference between the second pressure and the first pressure being lower than a lower threshold.

4. The method of claim 3, further comprising, regenerating the second filter by closing a switch of the electric circuit and flowing electricity through the second filter until the pressure difference between the second pressure and the first pressure is higher than an upper threshold.

5. The method of claim 1, further comprising, in response to the indication, limiting an engine speed or load.

6. The method of claim 1, wherein the indicating includes indicating degradation responsive to the interval between successive regenerations of the second filter being lower than a threshold duration.

7. The method of claim 6, wherein the interval is measured from initiation of a first regeneration event of the second filter to initiation of a second, immediately subsequent regeneration event of the second filter.

8. The method of claim 1, wherein the first filter is a diesel or gasoline particulate matter filter having a first, higher soot capacity, and wherein the second filter is a metal filter having a second, lower soot capacity, and wherein the indicating includes indicating the first filter is leaking by setting a diagnostic code.

9. The method of claim 1, wherein the second filter is coupled upstream of the second pressure sensor, and wherein flowing exhaust towards the second pressure sensor includes:
    flowing exhaust from the exhaust pipe into an inlet pipe, from the inlet pipe into the passage, the inlet pipe converging with the passage at a location external to the exhaust pipe, and from the passage into the exhaust pipe via an outlet pipe, the passage converging into the outlet pipe at a location downstream of the second pressure sensor and external to the exhaust pipe.

10. The method of claim 1, wherein a direction of flowing exhaust through the inlet pipe and the outlet pipe is perpendicular to a direction of exhaust flow through each of the exhaust pipe and the passage.

11. An engine exhaust system, comprising:
    an exhaust pipe including a first particulate filter;
    a soot detection system including an inlet pipe and an outlet pipe coupled to the exhaust pipe, downstream of the first particulate filter, the inlet pipe merging into a passage external to the exhaust pipe, the outlet pipe merging out of the passage external to the exhaust pipe;
    a second particulate filter coupled to the passage between the inlet pipe and the outlet pipe, the second particulate filter coupled to a source of electricity via a switch;
    a first pressure sensor at a first location in the exhaust pipe;
    a second pressure sensor at a second location in the passage external to the exhaust pipe; and
    a controller with computer readable instructions stored on non-transitory memory for:
        flowing a first portion of exhaust gas from downstream of the first filter towards the first pressure sensor;
        flowing a remaining portion of exhaust gas towards the second pressure sensor;
        regenerating the second filter based on output from first and the second pressure sensors; and
        adjusting engine operation based on a time elapsed between successive regenerations of the second filter.

12. The system of claim 11, wherein the inlet pipe comprises a plurality of perforations on a side of the inlet pipe within the exhaust pipe and proximate to the first filter, a diameter of the perforations sized to enable conglomerated particulates to impinge on a side of the inlet pipe within the exhaust pipe and distal to the first filter, the conglomerated particulates released from the inlet pipe into the exhaust pipe via a perforation on a bottom of the inlet pipe.

13. The system of claim 11, wherein the first location is downstream of the first filter in the exhaust pipe and the second location is downstream of the second filter in the passage external to the exhaust pipe.

14. The system of claim 11, wherein regenerating the second filter based on the pressure difference between the first location and the second location includes initiating regeneration of the second filter when the pressure difference is lower than a lower threshold, and terminating regeneration of the second filter when the pressure difference is higher than a upper threshold.

15. The system of claim 14, wherein adjusting engine operation based on a time elapsed between successive regenerations of the second filter includes regenerating the first filter when the time elapsed is higher than a threshold interval by retarding spark timing or enriching the exhaust gas, and indicating degradation of the first filter when the time elapsed is lower than the threshold interval.

16. The system of claim 15, further comprising ceasing regeneration of the first filter responsive to the indication of degradation.

17. A method, comprising:
    flowing exhaust gas from downstream of a particulate filter positioned in an engine exhaust conduit upstream of a first pressure sensor and a metal filter positioned upstream of a second pressure sensor in an exhaust bypass, the exhaust bypass external to the exhaust conduit, and adjusting engine operation based on degradation of the particulate filter, the degradation determined based on a time interval between a first regeneration and a second regeneration of the metal filter, the first regeneration and the second regeneration each performed based on a pressure difference between a pressure measured by the second pressure sensor and a pressure measured by the first pressure sensor.

18. The method of claim 17, wherein the adjusting includes:

in response to the time interval being greater than a threshold time interval, regenerating the particulate filter in the engine exhaust conduit when particulate filter regeneration conditions are met via one or more of a retarding spark and decreasing an air/fuel ratio; and in response to the time interval being less than the threshold time interval, indicating to an operator degradation of the particulate filter and adjusting an engine actuator to reduce engine torque output, wherein the threshold time interval is based on a time elapsed between completion of a regeneration event immediately preceding the first regeneration and completion of the first regeneration, and wherein the time interval between the first regeneration and the second regeneration of the metal filter includes a time elapsed between completion of the first regeneration and completion of the second regeneration.

19. The method of claim 17, wherein performing each of the first regeneration and the second regeneration based on the pressure difference includes regenerating the second filter when the pressure difference between the second location and the first location is lower than a lower threshold, and maintaining the regenerating until the pressure difference is higher than an upper threshold.

* * * * *